(12) United States Patent
Yokoyama

(10) Patent No.: US 9,970,119 B2
(45) Date of Patent: May 15, 2018

(54) CURVED GRATING STRUCTURE MANUFACTURING METHOD, CURVED GRATING STRUCTURE, GRATING UNIT, AND X-RAY IMAGING DEVICE

(71) Applicant: KONICA MINOLTA, INC., Chiyoda-ku (JP)

(72) Inventor: Mitsuru Yokoyama, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 208 days.

(21) Appl. No.: 15/031,598

(22) PCT Filed: Oct. 2, 2014

(86) PCT No.: PCT/JP2014/076460
§ 371 (c)(1),
(2) Date: Apr. 22, 2016

(87) PCT Pub. No.: WO2015/060093
PCT Pub. Date: Apr. 30, 2015

(65) Prior Publication Data
US 2016/0265125 A1  Sep. 15, 2016

(30) Foreign Application Priority Data

Oct. 25, 2013  (JP) ................. 2013-221986

(51) Int. Cl.
*A61B 6/00* (2006.01)
*G01N 23/00* (2006.01)
(Continued)

(52) U.S. Cl.
CPC .................. *C25D 1/00* (2013.01); *A61B 6/00* (2013.01); *A61B 6/40* (2013.01); *C25D 1/003* (2013.01);
(Continued)

(58) Field of Classification Search
CPC .............. A61B 6/06; A61B 6/40; A61B 6/484
See application file for complete search history.

(56) References Cited

U.S. PATENT DOCUMENTS

2011/0052800 A1  3/2011  Setomoto et al.
2011/0194673 A1  8/2011  Teshima et al.

FOREIGN PATENT DOCUMENTS

JP  2011-162854  8/2011
JP  2013-120126  6/2013
(Continued)

OTHER PUBLICATIONS

Search Report dated May 23, 2017 which issued in the corresponding European Patent Application No. 14855131.0.

*Primary Examiner* — Dani Fox
(74) *Attorney, Agent, or Firm* — Cozen O'Connor

(57) ABSTRACT

In one aspect, the present invention provides a curved grating structure manufacturing method which comprises: a grating forming step of forming, in one surface of a grating-forming workpiece, a grating region in which a plurality of members mutually having the same shape are periodically provided; a stress layer forming step of forming a stress layer capable of generating stress, on a grating plane-defining surface of the grating region; a boding step of bonding a support substrate to the stress layer; a polishing step of polishing the other surface of the grating-forming workpiece on a side opposite to the one surface having the support substrate bonded thereto; and a peeling step of peeling off the support substrate from the stress layer, wherein the polishing step includes performing the polishing to allow the grating-forming workpiece to be curved by a stress arising from the stress layer, after the peeling step.

8 Claims, 17 Drawing Sheets

(51) Int. Cl.
*C25D 1/00* (2006.01)
*C25D 5/02* (2006.01)
*C25D 7/00* (2006.01)
*C25D 7/12* (2006.01)
*G01T 7/00* (2006.01)
*G02B 5/18* (2006.01)
*G21K 1/06* (2006.01)
*C25D 5/10* (2006.01)
*C25D 5/48* (2006.01)
*G01N 23/205* (2018.01)
*A61B 6/06* (2006.01)

(52) U.S. Cl.
CPC ............ *C25D 5/02* (2013.01); *C25D 5/10* (2013.01); *C25D 5/48* (2013.01); *C25D 7/00* (2013.01); *C25D 7/12* (2013.01); *G01N 23/205* (2013.01); *G01T 7/00* (2013.01); *G02B 5/18* (2013.01); *G02B 5/1838* (2013.01); *G02B 5/1857* (2013.01); *G21K 1/06* (2013.01); *A61B 6/06* (2013.01); *A61B 6/484* (2013.01); *G21K 2207/005* (2013.01)

(56) References Cited

FOREIGN PATENT DOCUMENTS

| JP | 2013-134196 | 7/2013 |
| JP | 2014-190778 | 10/2014 |
| JP | 2014-190781 | 10/2014 |

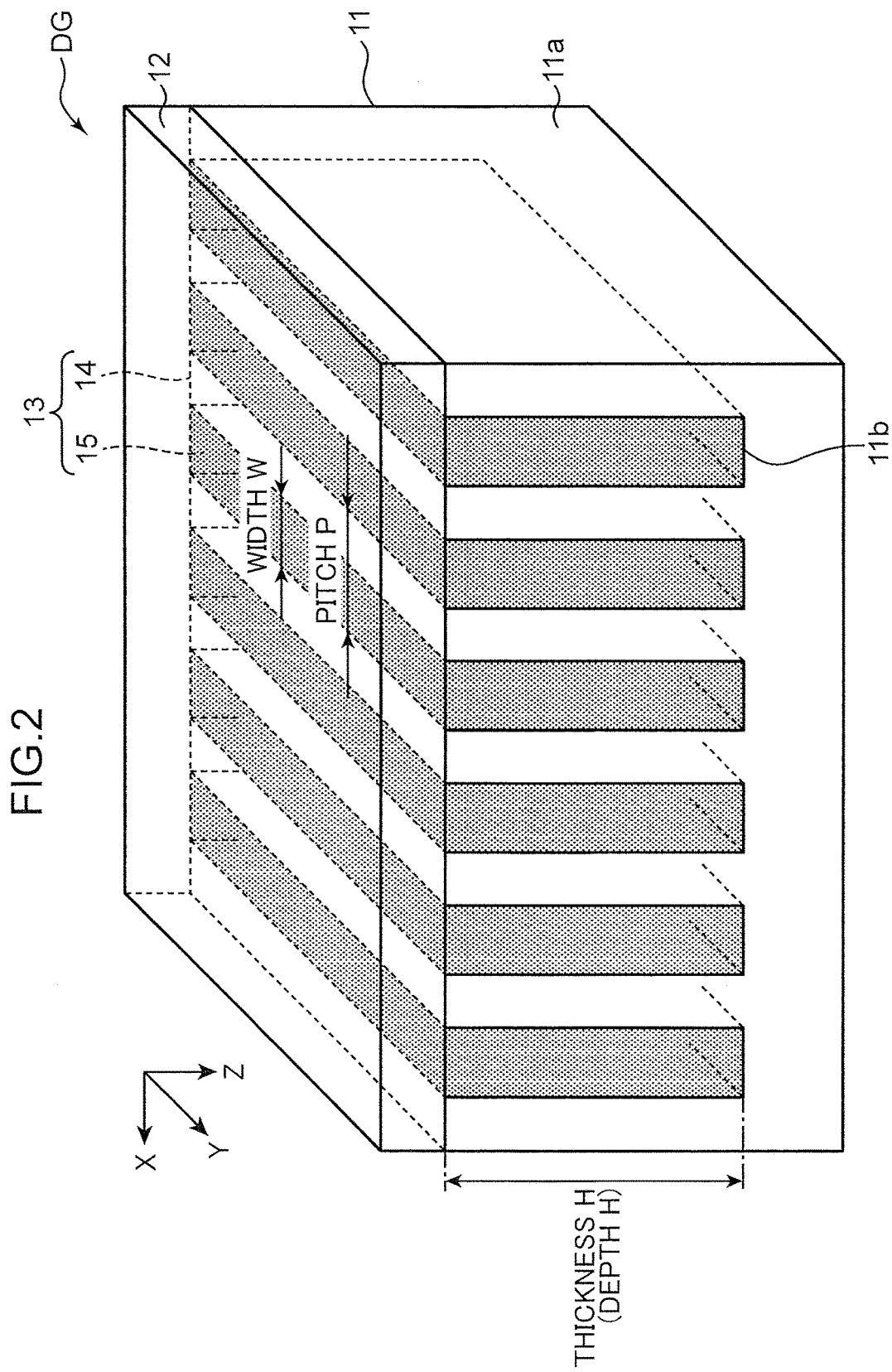

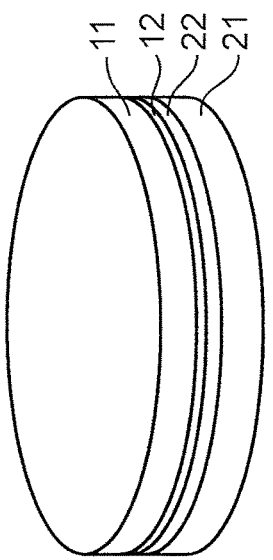
FIG.4A
FIG.4B
FIG.4C
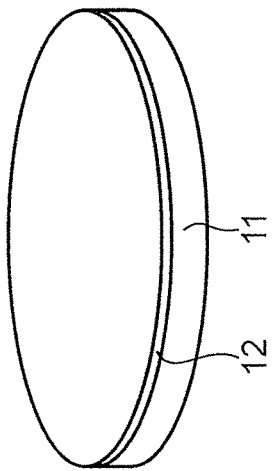
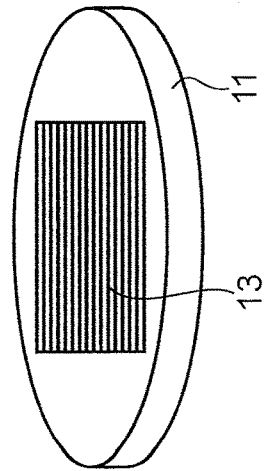
FIG.4D
FIG.4E
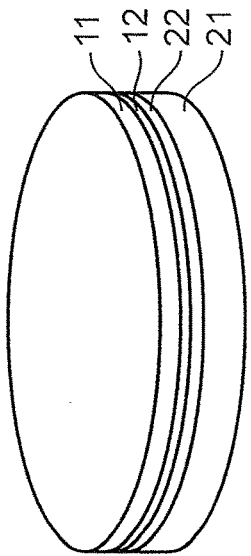
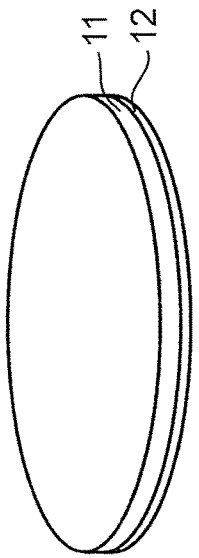

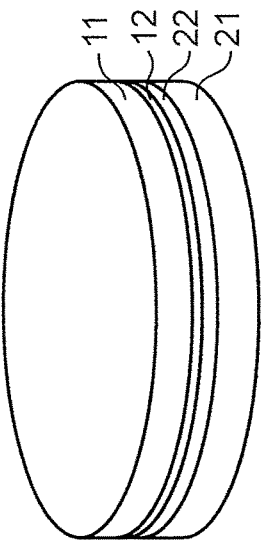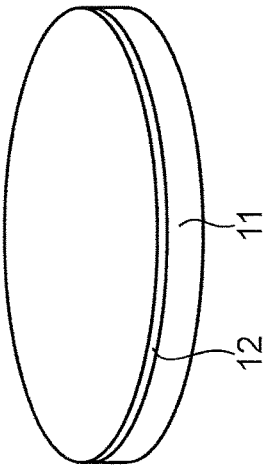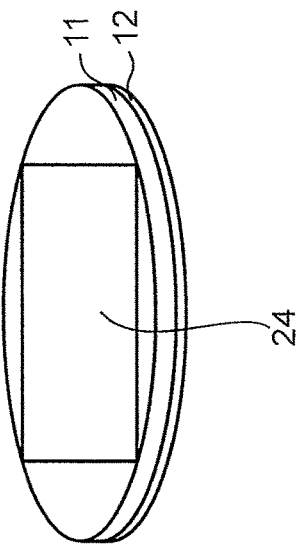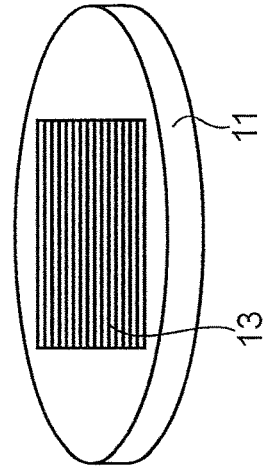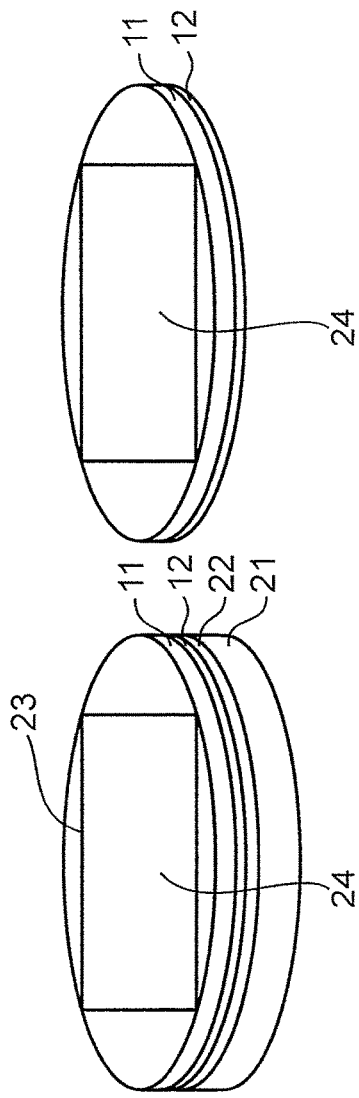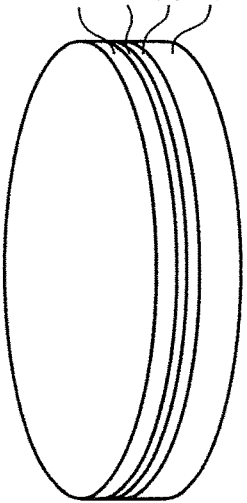

CURVED GRATING STRUCTURE MANUFACTURING METHOD, CURVED GRATING STRUCTURE, GRATING UNIT, AND X-RAY IMAGING DEVICE

RELATED APPLICATIONS

This is a U.S. National Phase Application under 35 USC 371 of International Application PCT/JP2014/076460 filed on Oct. 2, 2014.

This application claims the priority of Japanese application no. 2013-221986 filed Oct. 25, 2013, the entire content of which is hereby incorporated by reference.

TECHNICAL FIELD

The present invention relates to a manufacturing method for a curved grating structure having a curved-shaped periodic structure, and a curved grating structure manufactured by the manufacturing method. The present invention also relates to a grating unit constructed by arranging a plurality of the curved grating structures side-by-side, and an X-ray imaging device using the curved grating structure.

BACKGROUND ART

A diffraction grating is utilized in optical systems of various devices, as a spectral element having a periodic structure composed of a large number of parallel members, and, in recent years, its application to X-ray imaging devices has also been attempted. In terms of a diffraction process, the diffraction grating can be classified into a transmissive diffraction grating and a reflective diffraction grating. Further, the transmissive diffraction grating includes an amplitude-type diffraction grating (absorptive diffraction grating) in which a plurality of light-absorbing (absorptive) members are periodically arranged on a light-transmissive substrate, and a phase-type diffraction grating in which a plurality of optical phase-shifting members are periodically arranged on a light-transmissive substrate. As used herein, the term "absorption (absorptive)" means that light is absorbed by a diffraction grating at a rate of greater than 50%, and the term "transmission (transmissive)" means that light is transmitted through a diffraction grating at a rate of greater than 50%.

A diffraction grating for near infrared light, visible light, or ultraviolet light can be relatively easily produced, because near infrared light, visible light and ultraviolet light are sufficiently absorbed even by a thin metal. For example, an amplitude-type diffraction grating can be produced by subjecting a metal film formed on a substrate such as glass by vapor deposition to patterning to form a grating structure. In an amplitude-type diffraction grating for visible light, when aluminum (Al) is used as a metal, it is enough for the metal film to have a thickness, for example, of about 100 nm, because a transmittance of aluminum with respect to visible light, i.e., a transmittance of aluminum with respect to electromagnetic wave having a wavelength of about 400 nm to about 800 nm, is 0.001% or less.

On the other hand, as is well known, X-ray is very low in terms of absorption by a material, and is not so large in terms of phase shift, in general. Even in the case where an X-ray absorptive diffraction grating is produced using gold (Au) as a relatively favorable material, a required thickness of gold is about several ten μm or more. As above, in an X-ray diffraction grating, when a periodic structure is formed by arranging a transmissive member and an absorptive member or phase-shifting member which are even in width, at a pitch of several μm to several ten μm, a ratio of thickness to width (aspect ratio=thickness/width) in the gold portion has a high value of 5 or more.

Meanwhile, when a plurality of individual members constituting a periodic structure lie parallel to each other, X-rays enter a peripheral region of a diffraction grating obliquely, as depicted in FIG. 17A, because the diffraction grating has a high aspect ratio, as mentioned above, and an X-ray source for radiating X-rays is generally a spot wave source. Consequently, X-rays are not transmitted through the diffraction gating in the peripheral region, thereby leading to the occurrence of so-called "vignetting". As means to suppress the occurrence of vignetting, there is an idea of forming the members of the periodic structure to extend along respective light rays radiated from the spot wave source. Specifically, for example, it is conceivable to form a diffraction grating in a curved shape, as depicted in FIG. 17B.

Examples of a manufacturing method for a diffraction grating having such a curved periodic structure include a microstructural body manufacturing method described in the following Patent Literature 1. This microstructural body manufacturing method is a method for manufacturing a microstructural body comprising a mold which has a microstructure and a plated layer in an obverse side thereof and has a curved surface in a reverse side thereof. The method comprises the steps of: providing a mold having a microstructure formed by depthwise etching using anisotropic etching, wherein the mold is imparted with electrical conductivity at a bottom of a continuous gap in the microstructure; performing plating from the side of the bottom in the microstructure to form a first plated layer within the continuous gap in the microstructure; and forming a second plated layer capable of generating stress to cause the mold to become curved due to the stress arising from the second plated layer.

Meanwhile, in the microstructural body manufacturing method disclosed in the Patent Literature 1, when the mold is curved by the stress arising from the second plated layer, an excessively large thickness of the mold can cause an insufficient curvature. On the other hand, if a thin mold easy to be curved is employed, or the mold is thinned by polishing or the like before forming the second plated layer, in order to obtain a sufficient curvature, a problem such as breaking (crack) of the mold during manufacturing is more likely to occur. Further, in a situation where the mold is insufficiently curved due to an excessively large thickness thereof, it is conceivable to thin (reduce a thickness of) the insufficiently-curved mold by polishing to thereby allow the mold to become largely curved. However, this is not realistic because of difficulty in realizing desirable polishing. In such a manufacturing method using a stress layer such as the second plated layer, there is difficulty in manufacturing a grating structure largely (steeply) curved with a relatively small curvature radius, or a problem during manufacturing, such as crack of a grating structure during manufacturing, is more likely to occur. Therefore, there is a need for a manufacturing method capable of manufacturing a grating structure steeply curved with a relatively small curvature radius, while suppressing the occurrence of a problem during manufacturing of such a steeply curved grating structure, i.e., ensuring sufficiently high handleability.

CITATION LIST

Patent Literature

Patent Literature 1: JP 2011-162854A

SUMMARY OF INVENTION

The present invention has been made in view of the above circumstances, and an object thereof is to provide a curved grating structure manufacturing method capable of manufacturing a grating structure steeply curved with a relatively small curvature radius, while suppressing the occurrence of a problem during manufacturing thereof so as to ensure sufficiently high handleability, and a curved grating structure manufactured by the manufacturing method. It is another object of the present invention to provide a grating unit constructed by arranging a plurality of the curved grating structures side-by-side, and an X-ray imaging device using the curved grating structure.

In one aspect, the present invention provides a curved grating structure manufacturing method which comprises: a grating forming step of forming, in one surface of a grating-forming workpiece, a grating region in which a plurality of members mutually having a same shape are periodically provided; a stress layer forming step of forming a stress layer capable of generating stress, on a grating plane-defining surface of the grating region; a boding step of bonding a support substrate to the stress layer; a polishing step of polishing the other surface of the grating-forming workpiece on a side opposite to the one surface having the support substrate bonded thereto; and a peeling step of peeling off the support substrate from the stress layer, wherein the polishing step is configured to perform the polishing to allow the grating-forming workpiece to be curved by a stress arising from the stress layer, after the peeling step.

The above and other objects, features and advantages of the present invention will be apparent from the following detailed description and the accompanying drawings.

BRIEF DESCRIPTION OF DRAWINGS

FIG. 2 is a perspective view depicting the configuration of the curved grating structure according to the first embodiment.

FIGS. 4A to 4E are perspective views illustrating the manufacturing method for the curved grating structure according to the first embodiment.

FIGS. 6A to 6F are perspective views illustrating the another manufacturing method for the curved grating structure according to the first embodiment.

DESCRIPTION OF EMBODIMENTS

Based on the drawings, an embodiment of the present invention will now be described. It should be noted that elements or components assigned with the same reference sign in the figures means that they are the same elements or components, and duplicated descriptions thereof will be appropriately omitted.

First Embodiment: Curved Grating Structure

Figure 1:
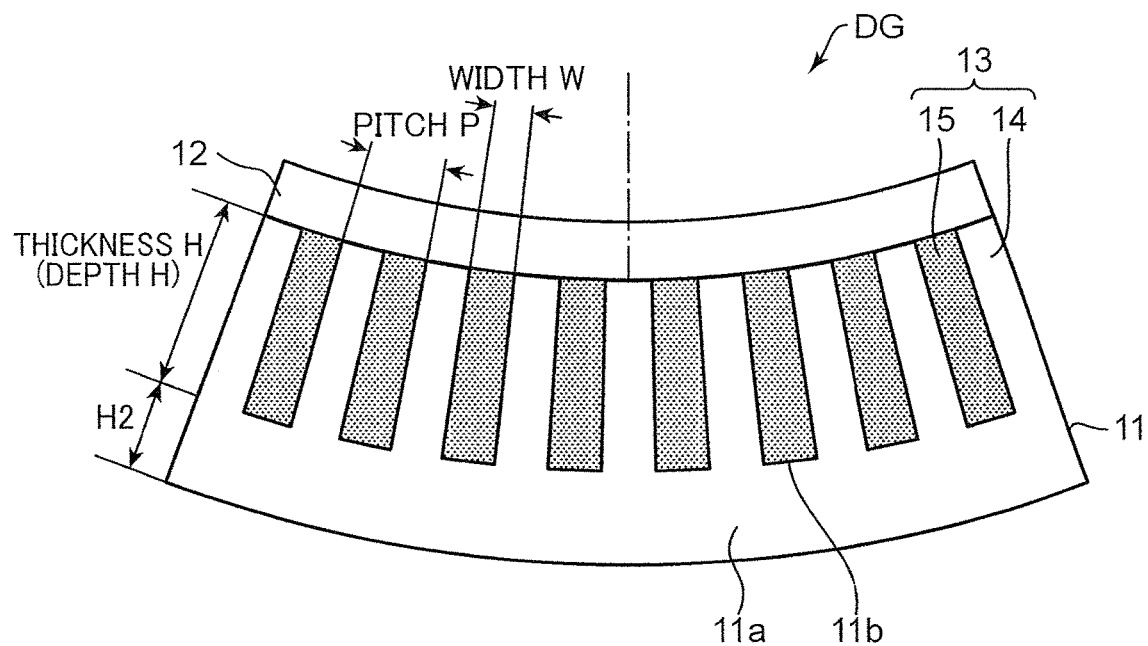
FIG. 1 is a sectional view depicting a configuration of a curved grating structure according to a first embodiment of the present invention.

FIG. 1 is a sectional view depicting a configuration of a curved grating structure according to a first embodiment of the present invention. FIG. 2 is a perspective view depicting the configuration of the curved grating structure according to the first embodiment. In FIG. 2, for the sake of illustration, an aftermentioned grating-forming workpiece 11 and an aftermentioned stress layer 12 are depicted in a flat state without being curved by stress. Actually, the grating-forming workpiece 11 and the stress layer 12 in an aftermentioned curved grating structure DG are curved by a stress, as depicted in FIG. 1.

As depicted in FIGS. 1 and 2, a curved grating structure DG according to the first embodiment comprises: a grating-forming workpiece 11 as a base material; a grating region 13 formed in one surface (one principal surface) of the grating-forming workpiece 11; and a stress layer 12 formed on a surface of the grating region (grating plane). It should be noted that, as long as the stress layer 12 is formed on the grating plane-defining surface of the grating region 13, it may be formed only on the grating plane-defining surface of the grating region 13, or may be formed on an entirety of the one surface of the grating-forming workpiece 11, as depicted in FIGS. 1 and 2.

The grating-forming workpiece 11 is a plate-shaped member which is formed of a given material and curved. For example, in the case where the curved grating structure DG is used as an X-ray grating structure as in this embodiment, the grating-forming workpiece 11 is formed of a given material having an X-ray transmissive or absorptive property. Thus, the grating-forming workpiece 11 may be formed of an appropriate material, depending on an intended use of the curved grating structure DG. In this embodiment, the grating-forming workpiece 11 is formed of a semiconductor having an X-ray transmissive property, such as silicon (Si), and is composed, for example, of a silicon wafer (silicon substrate). The grating-forming workpiece 11 is curved by a stress arising from an interaction with the stress layer 12. Thus, in a stress-free state, the grating-forming workpiece 11 is a flat plate-shaped member.

The grating region 13 is a region which is formed in one principal surface of the grating-forming workpiece 11 and in which a plurality of members 14 mutually having the same shape are periodically provided. That is, the grating region 13 comprises the plurality of members 14. In this embodiment, the curved grating structure DG is also used as an X-ray diffraction grating. Thus, as depicted in FIGS. 1 and 2, the grating region 13 comprises: a plurality of plate (layer)-shaped members (structural portions) 14 arranged such that principal surfaces thereof lie in opposed and approximately parallel relation to each other, at given intervals (pitch) P; and a plurality of remaining portions 15 each sandwiched between adjacent two of the structural portions 14. The curved grating structure DG only needs to comprise the plurality of members 14, and needs not comprise the remaining portions, depending on an intended use thereof or a type of diffraction grating. That is, each of the remaining portions may be a space or void. The grating region 13 is formed in the one principal surface of the curved grating-forming workpiece 11, so that it is curved depending on a curvature of the grating-forming workpiece 11.

The stress layer 12 is a layer capable of generating a given stress such as thermal stress. The stress layer 12 acts to generate a given stress in an interface between the grating-forming workpiece 11 and the stress layer 12. Thus, the grating-forming workpiece 11 is curved by a stress arising from the stress layer 12. Specifically, for example, in the case where a resin layer such as an ultraviolet curable resin is used as the stress layer 12, an uncured resin layer is formed on the grating-forming workpiece 11, and then when the resin layer is cured by ultraviolet irradiation or the like, the resin layer undergoes cure shrinkage. Due to a stress caused by the cure shrinkage, the grating-forming workpiece 11 is curved as depicted in FIG. 1. More specifically, in the curved grating structure according to this embodiment, the grating-forming workpiece 11 and the grating region 13 are curved such that the pitch P of the members (structural portions) becomes less (shorter) than that in the grating-forming workpiece 11 in a flat state, as depicted in FIG. 1. Alternatively, the curved grating structure according to this embodiment may be configured such that it is curved toward a side opposite to that depicted in FIG. 1. Specifically, the grating-forming workpiece 11 and the grating region 13 may be curved such that the pitch P of the members (structural portions) becomes greater (longer) than that in the grating-forming workpiece 11 in the flat state. It should be noted that, actually, in this embodiment, such curvature deformation does not substantially occur just by forming the stress layer 12, but occurs after an aftermentioned polishing or peeling step. On the other hand, in the case where the stress layer 12 is a type capable of generating a thermal stress, and the grating-forming workpiece 11 has a first thermal expansion coefficient $\alpha_1$, the stress layer 12 is composed of a layer having a second thermal expansion coefficient $\alpha_2$ different from the first thermal expansion coefficient $\alpha_1$. By forming the stress layer having such a different thermal expansion coefficient, in a situation where a difference occurs between a temperature at which the stress layer 12 is formed on the grating-forming workpiece 11, and a temperature at which the curved grating structure is actually used as a diffraction grating, the thermal stress is generated to cause the grating-forming workpiece 11 to become curved. This type of stress layer 12 may be any layer having the second thermal expansion coefficient $\alpha_2$ different from the first thermal expansion coefficient $\alpha_1$ of the grating-forming workpiece 11, and examples thereof include a quartz layer formed by a chemical vapor deposition (CVD) process or the like. Due to the given stress, the grating-forming workpiece 11 is curved as mentioned above. When the grating-forming workpiece 11 is formed of silicon, and the stress layer 12 is formed of quartz, the aforementioned curvature deformation toward a side opposite to that depicted in FIG. 1 can be achieved.

In this embodiment, the curvature occurs along a primary direction X which is a direction along which the plurality of members (structural portions) 14 are arranged side-by-side. Although the curvature may also occur along a secondary direction Y which is a direction orthogonal to the primary direction X, it should be limited to an extent that there is no influence on a Talbot interferometer or Talbot-Lau interferometer when a resulting curved grating structure is applied thereto.

As above, the grating region 13 is curved along the primary direction X, with a given curvature radius. However, in order to explain respective shapes of the structural portion 14 and the remaining portion 15 in more detail, the following description will be made on an assumption that the grating-forming workpiece 11 and the grating region 13 are in a flat state.

As mentioned above, the grating region 13 in this embodiment comprises the plurality of structural portions 14, and the plurality of remaining portions 15 which are a remaining part of the grating region 13 other than the plurality of structural portions 14. More specifically, in one aspect based on the above assumption, in the case of a one-dimensional grating structure as in the embodiment depicted in FIG. 2, when an XYZ orthogonal coordinate system is set as depicted in FIG. 2, the grating region 13 is formed on a plate- or layer-shaped portion (base plate portion) 11a along an X-Y plane of the grating-forming workpiece 11. In this grating region 13, each of the plurality of structural portions 14 has a given thickness H (a length in a Z direction perpendicular to an X-Y grating plane (a direction normal to the X-Y grating plane); a depth H) and linearly extends in a Y direction as a specific one of three mutually orthogonal directions, and each of the plurality of remaining portions 15 has the given thickness H and linearly extends in the Y direction. The plurality of structural portions 14 and the plurality of remaining portions 15 are alternately arranged in an X direction orthogonal to the Y direction, and in parallel to an X-Z plane whose normal direction is coincident with the X direction. Thus, the plurality of structural portions 14 are arranged at given intervals (pitch P), in the X direction orthogonal to the Y direction. In other words, the plurality of remaining portions 15 are arranged at given intervals (pitch P), in the X direction orthogonal to the Y direction as the specific direction. In this embodiment, the above given interval (pitch P) is set to a constant value. That is, the plurality of structural portions 14 (plurality of remaining portions 15) are arranged at even intervals P in the X direction orthogonal to the Y direction. In this embodiment, the structural portion 14 and the remaining portion 15 are made, respectively, of first and second grating region materials each having a respective one of mutually different first and second characteristic values of a given characteristic with respect to X-ray, wherein at least one of the first and second grating region materials is a metal.

In another aspect, more specifically, in the case of a one-dimensional grating structure as in the embodiment depicted in FIG. 2, by providing, in the grating-forming workpiece 11, a plurality of recesses 11b each having the given thickness H (depth H) and linearly extending in the Y direction as the specific direction, the plurality of structural portions 14 each having a given thickness H and linearly extending in the Y direction as the specific direction are formed to extend from the base plate portion 11a of the grating-forming workpiece 11 and stand vertically (in a -Z direction) from the base plate portion 11a of the grating-forming workpiece 11. Therefore, each of the plurality of recesses 11b is a plate- or layer-shaped space along a Y-Z plane orthogonal to the X-Y plane, and each of the plurality of structural portions 14 is a plate- or layer-shaped member along the Y-Z plane orthogonal to the X-Y plane. Thus, the plurality of recesses 11b and the plurality of structural portions 14 are alternately arranged in the X direction orthogonal to the Y direction, and in parallel to the Y-Z plane whose normal direction is coincident with the X direction. The plurality of structural portions 14 are arranged at given intervals P in the X direction orthogonal to the Y direction. In other words, the plurality of recesses 11b are arranged at given intervals P in the X direction orthogonal to the Y direction. In this embodiment, the given interval (pitch) P is set to a constant value. That is, the plurality of structural portions 14 (plurality of recesses 11b) are arranged at even intervals P in the X direction orthogonal to the Y direction. Then, in this embodiment, each of the plurality of remaining portions 15 is provided within a respective one of the plurality of recesses 11b, wherein the structural portion 14 is formed of a first grating region material, i.e., a material of the grating-forming workpiece 11, having a first value of a given characteristic with respect to X-ray, and the remaining portion 15 is formed of a second grating region material having a second value different from the first value, wherein at least one of the first grating region material and the second grating region material is a metal. In the above description, for the sake of simplicity of explanation, a plurality of portions each extending from the base plate portion 11a are described as the plurality of structural portions 14, and a plurality of portions each provided within a respective one of the recesses 11b are described as the plurality of remaining portions 15. Alternatively, a plurality of portions each extending from the base plate portion 11a may be referred to as "plurality of remaining portions 15", and a plurality of portions each provided within a respective one of the recesses 11b may be referred to as "plurality of structural portions 14".

In one example, the given characteristic with respect to X-ray is an X-ray transmittance (X-ray absorptance). In this case, a group of the plurality of structural portions 14 and a group of the plurality of remaining portions 15 function to transmit (or absorb) X-rays at different transmittances (or absorptances). The curved grating structure in this embodiment is used as an X-ray diffraction grating. Thus, in one aspect, the curved grating structure DG can be constructed to function as an amplitude-type diffraction grating by appropriately setting the thickness H of each of the plurality of structural portions 14, the thickness H of each of the plurality of remaining portions 15 and the given interval (pitch) P, depending on a wavelength of X-rays so as to satisfy X-ray diffraction conditions.

In another example, the given characteristic with respect to X-ray is an X-ray phase shift rate. In this case, respective groups of the plurality of structural portions 14 and the plurality of remaining portions 15 function to act to X-rays at different phase shift rates. Thus, in one aspect, the curved grating structure DG can be constructed to function as a phase-type diffraction grating by appropriately setting the thickness H of each of the plurality of structural portions 14, the thickness H of each of the plurality of remaining portions 15 and the given interval (pitch) P, depending on a wavelength of X-rays so as to satisfy X-ray diffraction conditions.

While the first grating region material of the structural portions 14 (the material of the grating-forming workpiece 11) may be arbitrary, it is preferably a type having a relatively small value of the given characteristic with respect to X-ray. Examples of the first grating region material include silicon, glass, resin, and a metal (including alloy) of an element having a relatively small atomic weight (relatively light element). From a viewpoint of being capable of forming a high-aspect ratio recess 11d at relatively high dimensional accuracy and in a relatively easy manner, the first grating region material is preferably silicon.

While the second grating region material of the remaining portions 15 may be arbitrary, it is preferably a type having a relatively large value of the given characteristic with respect to X-ray, from a viewpoint of being capable of reducing the thickness H of each of the remaining portions 15, i.e., the depth H of each of the remaining portions 15, so as to reduce the aspect ratio. For example, the second grating region material preferably contains a metal of an element having a relatively large atomic weight (relatively heavy element), specifically, at least one selected from the group consisting of gold (Au), platinum (Pt), iridium (Ir) and rhodium (Rh). By forming the remaining portions 15 using such a material, the remaining portions 15 can relatively largely act to X-rays, so that it becomes possible to further reduce the depth of each of the remaining portions 15 to thereby more facilitate the manufacturing of the curved grating structure DG.

The aspect ratio means a ratio of the thickness H (depth H) to a width W of each of the remaining portions 15 (or each of the recesses 11b) (in FIG. 1, it denotes a width of each of the remaining portions 15) (the aspect ratio=thickness H/width W). In the curved grating structure DG, each of the remaining portions 15 is formed with a high aspect ratio, for example, of 5 or more. The width W of the remaining portion 15 is a length of the remaining portion 15 in the X direction (width direction) orthogonal to the Y direction as the specific direction (longitudinal direction), and the thickness of the remaining portion 15 is a length of the remaining portion 15 in the Z direction (depth direction) normal to the plane defined by the Y direction and the X direction orthogonal to the X direction.

The above description of the grating region is based on the assumption that the grating-forming workpiece 11 and the grating region 13 are in a flat state, as mentioned above. On the other hand, a shape of the grating-forming workpiece 11 having the grating region 13 described based on the above assumption corresponds to a shape of the grating-forming workpiece before being curved. It should be noted that the grating-forming workpiece 11 may be constructed such that the structural portion 14 is in contact with the remaining portion 15, as depicted in FIG. 2, or may be constructed such that a void space (air gap) is provided between the structural portion 14 and the remaining portion 15, as described later.

A manufacturing method for the curved grating structure DG according to the first embodiment will be described below.

The curved grating structure DG according to the first embodiment can be manufactured, for example, by implementing the following steps. Specifically, the curved grating structure manufacturing method comprises: a grating forming step of forming, in one surface of a grating-forming workpiece, a grating region in which a plurality of members mutually having the same shape are periodically provided; a stress layer forming step of forming a stress layer capable of generating stress, on a grating plane-defining surface of the grating region; a boding step of bonding a support substrate to the stress layer; a polishing step of polishing the other surface of the grating-forming workpiece on a side opposite to the one surface having the support substrate bonded thereto; and a peeling step of peeling off the support substrate from the stress layer, wherein the polishing step is configured to perform the polishing to allow the grating-forming workpiece to be curved by a stress arising from the stress layer, after the peeling step.

This manufacturing method makes it possible to manufacture a grating structure steeply curved with a relatively small curvature radius. This manufacturing method also makes it possible to sufficiently suppress the occurrence of a problem during manufacturing thereof so as to ensure sufficiently high handleability.

Examples of the manufacturing method include the following method.

FIGS. 3A to 3E are sectional views illustrating a manufacturing method for the curved grating structure according to the first embodiment. FIGS. 4A to 4E are perspective views illustrating the manufacturing method for the curved grating structure according to the first embodiment.

Figure 3A:
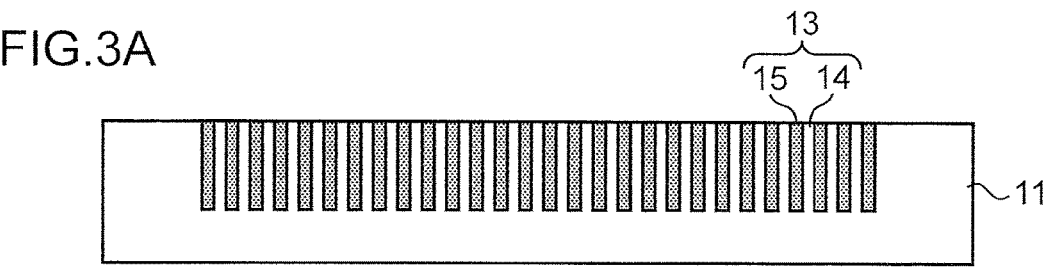
FIGS. 3A to 3E are sectional views illustrating a manufacturing method for the curved grating structure according to the first embodiment.

First of all, as depicted in FIGS. 3A and 4A, a grating-forming workpiece 11 is prepared which has a grating region 13 formed in one surface thereof in such a manner that a plurality of members (structural portions) 14 mutually having the same shape are periodically provided therein. That is, an initial grating-forming workpiece 11 is subjected to the grating forming step of forming, in one surface thereof, the grating region 13 in which the plurality of members 14 mutually having the same shape are periodically provided is implemented. This step will be described in detail later. As depicted in FIGS. 1 and 2, in this embodiment, the grating region 13 comprises: a plurality of plate (layer)-shaped members (structural portions) 14 arranged such that principal surfaces thereof lie in opposed and approximately parallel relation to each other, at given intervals (pitch) P; and a plurality of remaining portions 15 each sandwiched between adjacent two of the structural portions 14. The method may comprise a step of disposing a metal portion between adjacent two of the members 14 formed in the grating forming step. Specifically, examples of the grating-forming workpiece 11 provided for the following steps include the following workpiece. As a specific example, a metal grating structure having a plurality of remaining portions formed of gold as metal may be used. More specifically, a metal grating structure may be used which is obtained by: forming a plurality of grooves each having a depth H of 125 μm, in a 130 mm-square region approximately inscribed in a 725 μm-thick, 8-inch silicon substrate, at intervals (pitch) P of 5.3 μm; and filling the grooves with gold through an electroforming process (electroplating process). Alternatively, a metal grating structure may also be used which is obtained by: forming a plurality of grooves each having a depth H of 150 μm, in a 100 mm-square region approximately inscribed in a 625 μm-thick, 6-inch silicon substrate, at intervals (pitch) P of 22.8 μm; and filling the grooves with gold through an electroforming process (electroplating process).

Figure 3B:
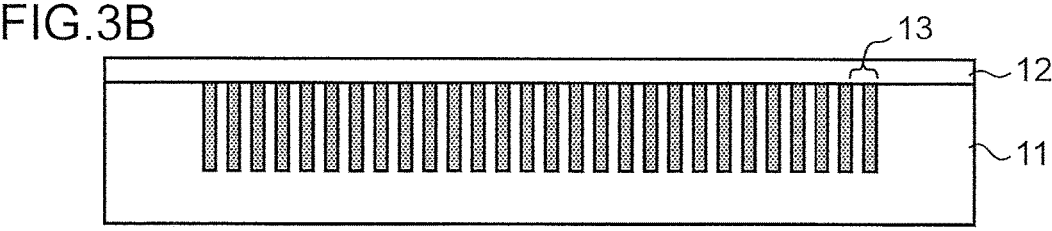

Subsequently, as depicted in FIGS. 3B and 4B, the resulting grating-forming workpiece 11 is subjected to the stress layer forming step of forming a stress layer 12 capable of generating stress, on a surface (grating plane-defining surface) of the grating region 13. In this embodiment, the stress layer 12 is formed on an entirety of the other principal surface of the grating-forming workpiece 11 on a side opposite to the one principal surface (one surface) thereof.

In the manufacturing method pertaining to this embodiment, the grating-forming workpiece 11 is not curved or almost not curved even after forming the stress layer 12 on the grating plane-defining surface of the grating region 13. That is, the grating-forming workpiece 11 before being subjected to the polishing step has rigidity enough to be substantially kept from being curved by a stress from the stress layer 12. Specifically, the grating-forming workpiece 11 before being subjected to the polishing step has a thickness equal to or greater than a thickness which substantially prevents curvature deformation due to a stress from the stress layer 12. Further, the grating-forming workpiece 11 having a thickness enough to suppress curvature deformation due to the stress layer 12 at a time before it is subjected to the polishing step is desirable from a viewpoint of being capable of suppressing the occurrence of a problem during manufacturing, such as crack.

The stress layer 12 is a layer capable of generating a given stress such as thermal stress, as mentioned above. In this embodiment, the stress layer 12 is a layer capable of being relatively shrunk with respect to the grating-forming workpiece 11. Specific examples of the stress layer 12 include a resin layer such as an ultraviolet curable resin. Specific examples of the stress layer forming step as a process for forming the stress layer include a process of applying a resin composition containing an ultraviolet curable resin, on the surface (grating plane-defining surface) formed with the grooves, at a given thickness, and curing the applied resin composition by means of ultraviolet irradiation, thereby forming a resin layer. In this process, during curing, the resin composition undergoes cure shrinkage. Then, a stress caused by the cure shrinkage becomes effective. In the case where the ultraviolet curable resin is a liquid form, only the ultraviolet curable resin may be applied. For example, as the ultraviolet curable resin, it is possible to use an ultraviolet curable resin 3026E produced by ThreeBond Co., Ltd. In the case of using the 3026E, after applying the resin onto the grating plane-defining surface, at a thickness of 50 μm, it is cured by ultraviolet irradiation. During the curing, the 3026E is shrunk by about 7.5 volume %.

Other specific examples of the stress layer forming step include a process of forming, as the stress layer 12, a quartz layer on the surface (grating plane-defining surface) formed with the grooves, at a film thickness, for example, of 12 μm, by a plasma CVD process using TEOS gas under a high film-forming temperature, for example, of 300° C. In this process, assuming that the grating-forming workpiece 11 is formed of silicon, and, after the film formation, the temperature is returned to normal temperature, silicon is shrunk more largely than quartz, because silicon has a thermal expansion coefficient greater than that of quartz, so that the grating-forming workpiece 11 is curved toward a side opposite to that depicted in FIG. 3E.

As regards a purpose of obtaining a stress layer having a thickness enough to allow the grating-forming workpiece after being subjected to the polishing step to be curved, the process of forming a resin layer by application of a resin composition can achieve the purpose within a short period of time, as compared to the process of forming a quartz layer by a CVD process or the like.

In this embodiment, the stress layer 12 is formed on the grating plane-defining surface. This is desirable from a viewpoint of being capable of manufacturing or obtaining a curved grating structure which is kept from exposure of the grating plane-defining surface and thus suppressed from occurrence of damage.

Figure 3C:
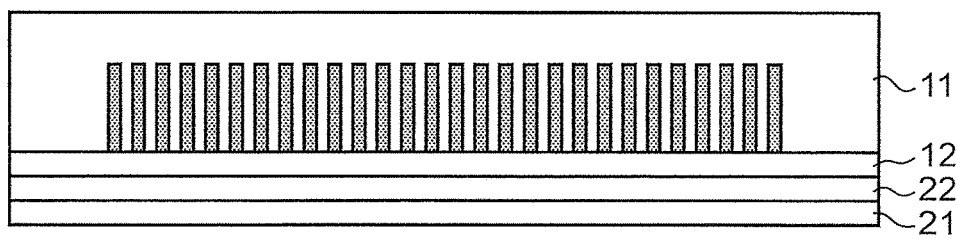

Subsequently, as depicted in FIGS. 3C and 4C, the obtained intermediate product is subjected to the boding step of bonding a support substrate 21 to the stress layer 12. That is, the manufacturing method pertaining to this embodiment is not intended that, although a curvature of the grating-forming workpiece 11 is still insufficient even after the stress layer is formed on the grating plane-defining surface of the grating region 13, the grating-forming workpiece 11 is thinned by polishing or the like just after forming the stress layer 12, thereby causing the grating-forming workpiece 11 to become curved. Instead, in the manufacturing method pertaining to this embodiment, a support substrate 21 inhibiting curvature deformation of the grating-forming workpiece 11 is bonded to the stress layer 12. FIGS. 3C and 4C depict the grating-forming workpiece upside down with respect to the grating-forming workpiece depicted in FIGS. 3B and 4B.

The support substrate 21 functions to, in a state in which it is bonded to the stress layer 12 on the grating-forming workpiece 11, inhibit curvature deformation of the grating-forming workpiece 11 to an extent enough to prevent the grating-forming workpiece 11 from being curved to hinder desirable polishing, during polishing in the aftermentioned polishing step. Preferably, the support substrate 21 is capable of, in the state in which it is bonded to the stress layer 12 on the grating-forming workpiece 11, realizing a situation where the grating-forming workpiece 11 is not curved or almost not curved by a stress from the stress layer even after the grating-forming workpiece 11 is thinned through the aftermentioned polishing step. Specific examples of the support substrate 21 include a glass substrate having a thickness of 3 mm. More specifically, when an 8-inch silicon substrate is used as the grating-forming workpiece 11, an 8-inch glass substrate may be used as the support substrate 21, and, when a 6-inch silicon substrate is used as the grating-forming workpiece 11, a 6-inch glass substrate may be used as the support substrate 21.

Preferably, the bonding step is configured to bond the stress layer 12 and the support substrate 21 together through a tacky adhesive layer 22. This tacky adhesive layer 22 needs to have adhesiveness capable of preventing the support substrate 21 from being peeled off from the stress layer 12 even when the grating-forming workpiece 11 is urged to be curved. On the other hand, from a viewpoint of facilitating peeling in the aftermentioned peeling step so as to suppress the occurrence of damage during the peeling, the tacky adhesive layer 22 preferably has ability that a tacky adhesive force thereof is lowered in an easy manner.

Specifically, the tacky adhesive layer 22 lies on the support substrate 21, and intervenes between the stress layer 12 and the support substrate 21 during bonding between the stress layer 12 and the support substrate 21. Specific examples of the tacky adhesive layer 22 include a type having ability that adhesiveness thereof is deteriorated by heating or ultraviolet irradiation. Assume that the tacky adhesive layer 22 is composed of a type having ability that adhesiveness thereof is deteriorated by ultraviolet irradiation. In this case, during the aftermentioned peeling step, when ultraviolet rays are radiated from the side of the support substrate 21, the radiated ultraviolet rays can reach the tacky adhesive layer to cause deterioration in adhesiveness. More specifically, as an example of the tacky adhesive layer 22 having ability that adhesiveness thereof is deteriorated by ultraviolet irradiation, it is possible to use a UV release sheet (Adwill (two-sided adhesive type) produced by Lintec Corporation). On the other hand, as an example of the tacky adhesive layer 22 having ability that adhesiveness thereof is deteriorated by heating, it is possible to use a heat release sheet (REVALPHA produced by Nitto Denko Corporation).

Figure 3D:
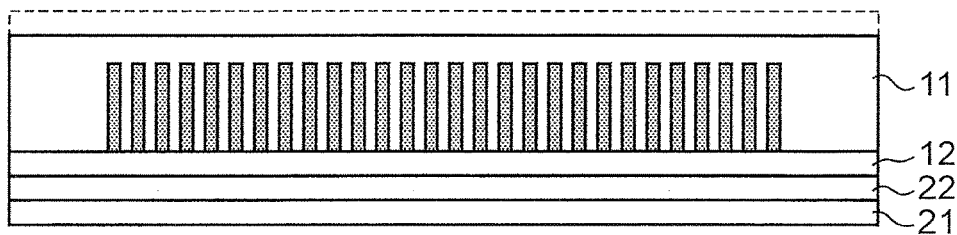

Subsequently, as depicted in FIGS. 3D and 4D, the obtained intermediate product is subjected to the polishing step of polishing the other surface of the grating-forming workpiece 11 on the side opposite to the one surface having the support substrate 21 bonded thereto. That is, in the polishing step, a surface of the grating-forming workpiece 11 on the back side of the grating region 13 is subjected to polishing. The polishing step is configured to perform the polishing to allow the grating-forming workpiece 11 to be curved by a stress arising from the stress layer 12, after the aftermentioned peeling step. That is, the polishing step is configured to perform the polishing such that the grating-forming workpiece 11 after being subjected to the polishing step has rigidity (thickness) enough to be permitted to be curved by a stress arising from the stress layer 12. Specifically, the grating-forming workpiece 11 after being subjected to the polishing step has a thickness equal to or less than a thickness which permits curvature deformation due to a stress from the stress layer 12.

In the manufacturing method pertaining to this embodiment, the support substrate 21 is bonded to the stress layer 12. Thus, during the polishing, the grating-forming workpiece 11 is not curved or almost not curved by a stress arising from the stress layer 12. Therefore, it becomes possible to sufficiently suppress hindering of the polishing due curvature deformation of the grating-forming workpiece 11, to realize desirable polishing. As a result of the polishing, upon peeling the support substrate 21, the grating-forming workpiece 11 is largely curved. However, before peeling the support substrate 21 even after completion of the polishing, curvature deformation of the grating-forming workpiece 11 is suppressed by the bonded support substrate 21.

A polishing process in the polishing step is not particularly limited, as long as it is capable of polishing the grating-forming workpiece 11.

Figure 3E:
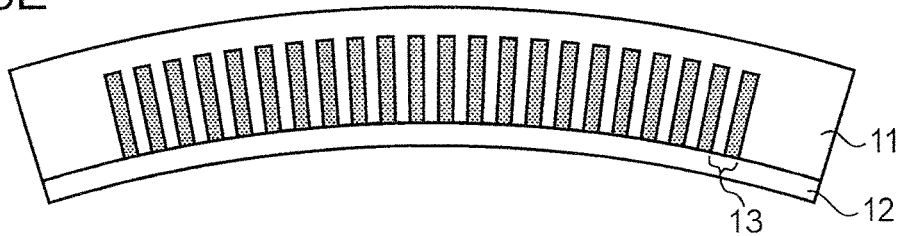

Subsequently, the obtained intermediate product is subjected to the peeling step of peeling off the support substrate 21 from the stress layer 12. As a result, the grating-forming workpiece 11 is curved to obtain a curved grating structure, as depicted in FIGS. 3E and 4E. That is, the grating-forming workpiece 11 is formed in a thinned structure easy to be curved, through the polishing step, and the support substrate 21 inhibiting curvature deformation of the grating-forming workpiece 11 is peeled off, so that the grating-forming workpiece 11 is largely curved to obtain a curved grating structure steeply curved with a relatively small curvature radius.

In FIG. 4E, for the sake of illustration, each of the grating-forming workpiece 11 and the stress layer 12 is depicted in a flat state without being curved by stress. However, actually, as illustrated in FIG. 3E, the grating-forming workpiece 11 and the stress layer 12 in the curved grating structure DG are curved by stress.

A peeling process in the peeling step is not particularly limited, as long as it is capable of peeling off the support substrate 21 from the stress layer 12. In the case where the support substrate 21 is bonded using a tacky adhesive layer having ability that a tacky adhesive force thereof is lowered by heating, the peeling may be performed after a heating treatment. On the other hand, in the case where the support substrate 21 is used with a tacky adhesive layer having ability that a tacky adhesive force thereof is lowered by ultraviolet irradiation, the peeling may be performed after ultraviolet irradiation through the support substrate.

The above manufacturing method makes it possible to obtain a curved grating structure steeply curved with a relatively small curvature radius as mentioned above. In the above manufacturing method, the grating-forming workpiece 11 is thinned to an extent enough to be permitted to be curved, after the polishing step, and is actually curved after the peeling step. This makes it possible to minimize an operation to be performed in a situation where the grating-forming workpiece is thinned or curved, thereby sufficiently suppressing the occurrence of a problem such as crack of the grating-forming workpiece during manufacturing. In addition, the above manufacturing method makes it possible to realize desirable polishing in the polishing step, as mentioned above.

In the above manufacturing method, it is possible to variously select and combine conditions in the respective steps. As one example, in the case of using a grating-forming workpiece obtained by forming a plurality of grooves each having a depth H of 125 µm, in a 725 µm-thick, 8-inch silicon substrate, when the aforementioned process of forming a quartz layer at a thickness of 12 µm by a CVD process at a temperature of 300° C. is used as the stress layer forming step, and the polishing in the polishing step is performed until a thickness of the grating-forming workpiece becomes 225 µm, a grating structure is obtained in which a plurality of structural portions and a plurality of remaining portions each having a thickness H of 125 µm are formed on a base plate portion having a thickness of 100 µm. When the thicknesses are set as above, a finally obtained curved grating structure is curved with a curvature radius of 1350 mm. As another example, in the case of using a grating-forming workpiece obtained by forming a plurality of grooves each having a depth H of 150 µm, in a 625 µm-thick, 6-inch silicon substrate, when the aforementioned process of forming a resin layer (ultraviolet curable resin 3026E produced by ThreeBond Co., Ltd) at a thickness of 50 µm is used as the stress layer forming step, and the polishing in the polishing step is performed until a thickness of the grating-forming workpiece becomes 200 µm, a grating structure is obtained in which a plurality of structural portions and a plurality of remaining portions each having a thickness H of 150 µm are formed on a base plate portion having a thickness of 50 µm. When the thicknesses are set as above, a finally obtained curved grating structure is curved with a curvature radius of 60 mm. In addition to the above examples, various other combinations of the type of the stress layer, the thickness of the stress layer and the thickness of the grating-forming workpiece are conceivable, depending on a required curvature radius and others.

In the above manufacturing method, the stress layer 12 is formed on the grating plane-defining surface of the grating-forming workpiece 11, and therefore the grating plane is maintained in a non-open state after formation of the stress layer 12, so that it becomes possible to suppress damage or the like to the grating region 13 during manufacturing.

In view of these, it is believed that the above manufacturing method makes it possible to manufacture a grating structure steeply curved with a relatively small curvature radius, while suppressing the occurrence of a problem during manufacturing thereof so as to ensure sufficiently high handleability.

In addition, in the finally obtained curved grating structure, the grating plane thereof is maintained in a non-open state by the stress layer 12, so that it becomes possible to suppress damage to the grating region.

The curved grating structure DG obtained by the above manufacturing method is steeply curved with a relatively small curvature radius, so that it becomes possible to prevent or reduce so-called "vignetting", even in the case of using a spot wave source. Further, this curved grating structure may be further curved. In this case, a distance with respect to a point wave source can be reduced, thereby facilitating downsizing of a device.

As mentioned above, the manufacturing method for the curved grating structure according to the first embodiment is capable of manufacturing a grating structure steeply curved with a relatively small curvature radius, while suppressing the occurrence of a problem during manufacturing thereof so as to ensure sufficiently high handleability.

Next, a manufacturing method capable of allowing a curved grating structure obtained after the peeling step to already have a desired shape, so as to provide excellent handleability will be described. In the aforementioned manufacturing method, there is a need to cut an obtained curved grating structure to have a desired shape, in some cases. During the cutting, there is a risk of the occurrence of crack or the like, because the curved grating structure is thinned through the polishing step. In this regard, the following manufacturing method can provide excellent handleability, because it allows a curved grating structure obtained after the peeling step to already have a desired shape. Further, the following manufacturing method can provide excellent handleability, from a viewpoint of being capable of suppressing the occurrence of crack due to cutting after the peeling step. Specifically, the following manufacturing method comprises, between the polishing step and the peeling step, i.e., just before the peeling step, a slitting step of forming a slit in the grating-forming workpiece 11 and the stress layer 12 to allow the grating-forming workpiece 11 and the stress layer 12 to have a desired shape in a state in which they are bonded to the support substrate 21. In this manufacturing method, a curved grating structure having a desired shape can be formed at a stage when it is peeled off from the support substrate in the peeling step.

Examples of this manufacturing method include the following method.

FIGS. 5A to 5F are sectional views illustrating another manufacturing method for the curved grating structure according to the first embodiment. FIGS. 6A to 6F are perspective views illustrating the another manufacturing method for the curved grating structure according to the first embodiment.

In this manufacturing method, first of all, as depicted in FIGS. 5A to 5D and 6A to 6D, a grating-forming workpiece is sequentially subjected to a grating forming step, a stress layer forming step, a boding step and a polishing step. These steps are the same as the grating forming step, the stress layer forming step, the boding step and the polishing step in the aforementioned manufacturing method. In this manufacturing method, the obtained intermediate product after being subjected to the polishing step is subjected to the slitting step. The obtained intermediate product after being subjected to the slitting step is subjected to a peeling step. This peeling step is the same as the peeling step in the aforementioned manufacturing method.

As depicted in FIGS. 5E to 6E, in the slitting step, a slit 23 is formed from the other surface of the grating-forming workpiece 11 in a normal direction with respect to the other surface, until reaching a depth equal to or greater than a total thickness of the grating-forming workpiece 11 and the stress layer 12. By forming the slit 23, a section 24 surrounded by the slit 23 is formed in the grating-forming workpiece 11 and the stress layer 12. That is, the slitting step is configured to form a slit 23 in the grating-forming workpiece 11 and the stress layer 12 in such a manner as to allow a section 24 surrounded by the slit 23 to have a desired shape. This slit 23 has a depth equal to or greater than a total thickness of the grating-forming workpiece 11 and the stress layer 12, and, preferably, has a depth less than a total thickness of the grating-forming workpiece 11, the stress layer 12, the support substrate 21 and the tacky adhesive layer 22. The depth of the slit 23 may be equal to or greater than the total thickness of the grating-forming workpiece 11, the stress layer 12, the support substrate 21 and the tacky adhesive layer 22. In this case, however, the grating-forming workpiece 11 is undesirably separated by the slit before the peeling step. Therefore, as long as the depth of the slit 23 is less than the total thickness of the grating-forming workpiece, the stress layer and the support substrate 21, and the tacky adhesive layer 22, it is possible to prevent the grating-forming workpiece 11 formed with the slit 23 to be separated into pieces, and thus provide further enhanced handleability.

A technique of forming the slit is not particularly limited. Examples of the slit forming technique include a technique of forming a slit using a blade dicer.

Figure 5A:
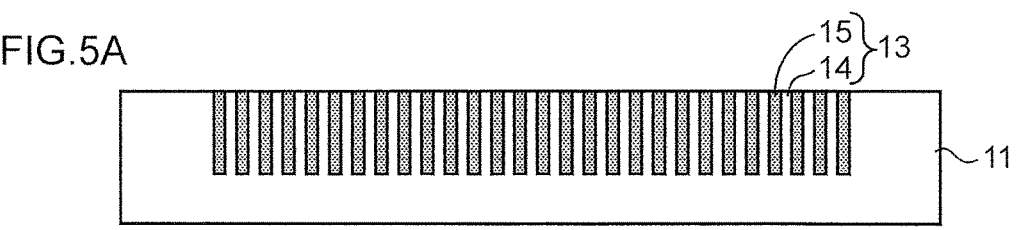
FIGS. 5A to 5F are sectional views illustrating another manufacturing method for the curved grating structure according to the first embodiment.
Figure 5B:
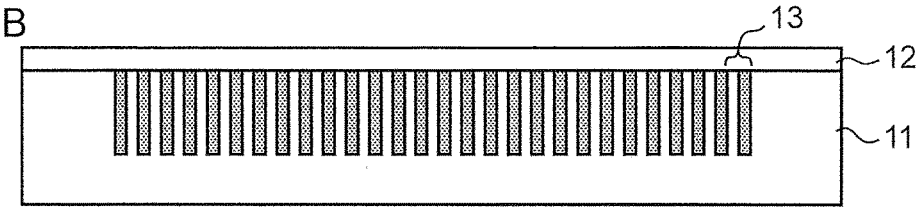
Figure 5C:
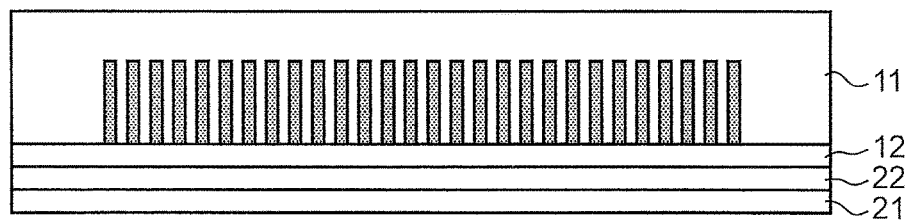
Figure 5D:
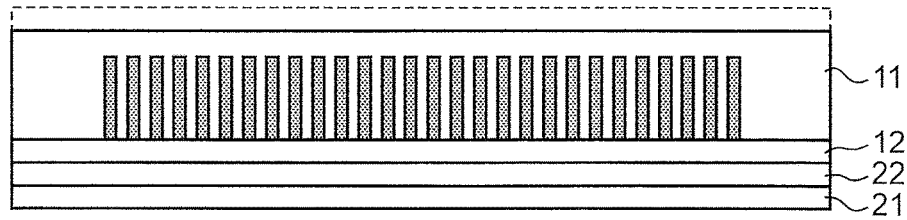
Figure 5E:
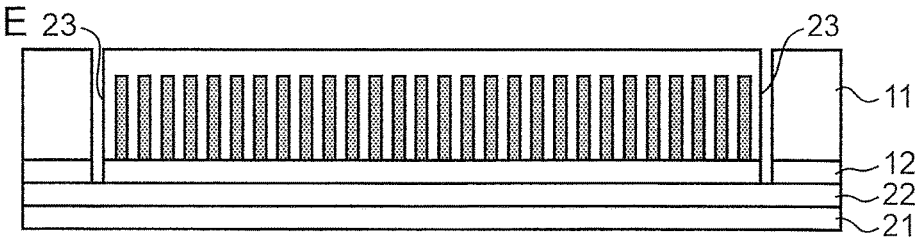
Figure 5F:
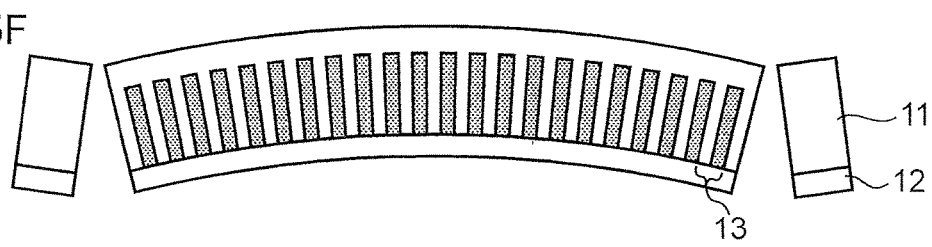

Subsequently, as depicted in FIGS. 5F and 6F, the obtained intermediate product is subjected to the peeling step. The section 24 surrounded by the slit 23 is formed in the grating-forming workpiece 11, so that the section 24 surrounded by the slit 23 is separated from the support substrate 21 through the peeling step. Thus, as a result of the peeling step, a curved grating structure having a desired shape is obtained.

In FIG. 6F, for the sake of illustration, each of the grating-forming workpiece 11 and the stress layer 12 is depicted in a flat state without being curved by stress. However, actually, as illustrated in FIG. 5F, the grating-forming workpiece 11 and the stress layer 12 in the curved grating structure DG are curved by stress.

As above, by subjecting the intermediate product to the slitting step just before the peeling step, it becomes possible to omit cutting or the like of a curved grating structure after the peeling step. Thus, this curved grating structure manufacturing method can provide further enhanced handleability.

Next, another example of the slitting step will be described.

In the slitting step, the section 24 surrounded by the slit may be formed just one, as mentioned above. Alternatively, the section 24 surrounded by the slit may be formed plurally. This makes it possible to simultaneously manufacture a plurality of small-size curved grating structures each having a desired shape.

Specific examples of this manufacturing method include a method comprising the following step as such a slitting step.

Figure 7A:
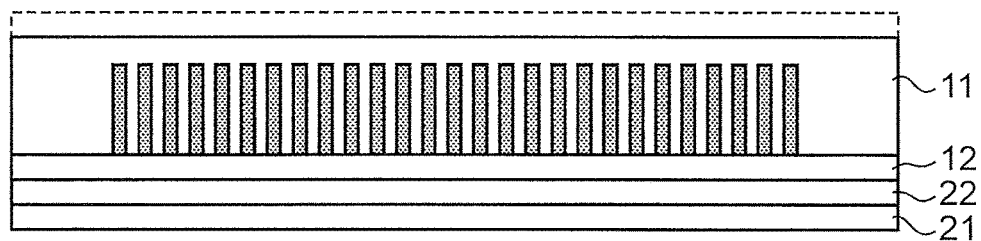
FIGS. 7A to 7C are sectional views illustrating yet another manufacturing method for the curved grating structure according to the first embodiment.
Figure 7B:
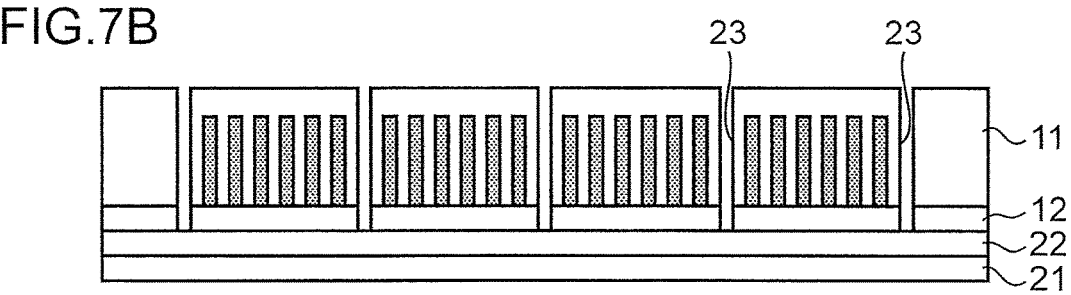
Figure 7C:
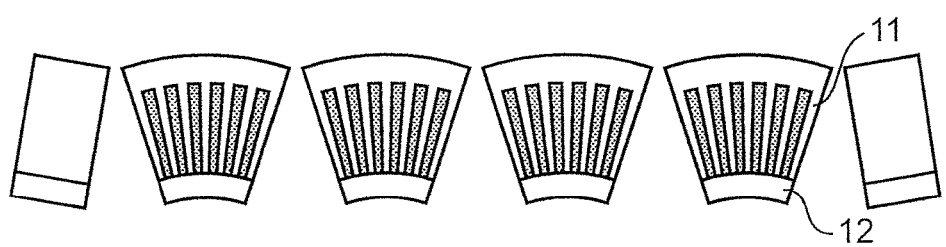
Figure 8B:
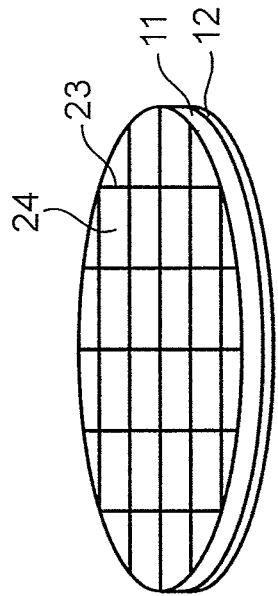
FIGS. 8A and 8B are perspective views illustrating the yet another manufacturing method for the curved grating structure according to the first embodiment.
Figure 8A:
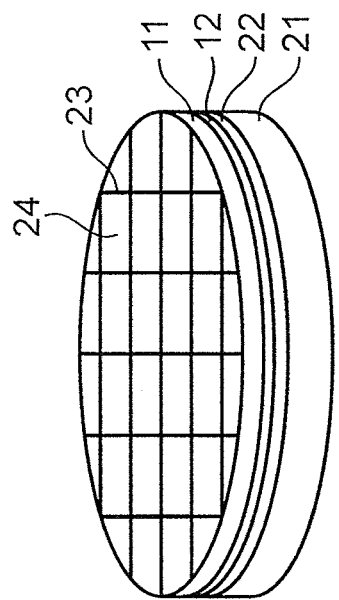

FIGS. 7A to 7C are sectional views illustrating yet another manufacturing method for the curved grating structure according to the first embodiment. FIGS. 8A and 8B are perspective view illustrating the yet another manufacturing method for the curved grating structure according to the first embodiment.

As depicted in FIGS. 7A to 8A, in this slitting step, a slit 23 is formed in the grating-forming workpiece 11 to form a plurality of sections 24 surrounded by the slit 23. This makes it possible to simultaneously manufacture a plurality of small-size curved grating structures each having a desired shape, as depicted in FIGS. 7A and 8B. Therefore, there is no need to cause a plurality of small-size grating structure to become curved one-by-one. On the other hand, in the case where a plurality of small-size grating structures are obtained before they are curved, it is necessary to cause the plurality of obtained small-size grating structures to become curved one-by-one. In the method pertaining to this embodiment, a plurality of small-size grating structures are obtained after they are curved, it is not necessary to cause each of the small-size grating structure to become curved individually.

As above, this manufacturing method makes it possible to simultaneously manufacture a plurality of small-size curved grating structures each having a desired shape, so as to provide excellent handleability. In addition, the slitting is performed in a flat state in which the support substrate is bonded. This makes it possible to suppress damage to a curved grating structure, as compared to the case where a curved grating structure obtained without being subjected to the slitting step is cut into a plurality of pieces.

In FIG. 8B, for the sake of illustration, each of the grating-forming workpiece 11 and the stress layer 12 is depicted in a flat state without being curved by stress. However, actually, as illustrated in FIG. 7A, the grating-forming workpiece 11 and the stress layer 12 in the curved grating structure DG are curved by stress.

Next, the grating-forming workpiece and the grating forming step will be described.

The grating forming step may be configured to form, in one surface of the grating-forming workpiece 11, the grating region 13 in which the plurality of members 14 mutually having the same shape are periodically provided, as mentioned above.

Figure 9:
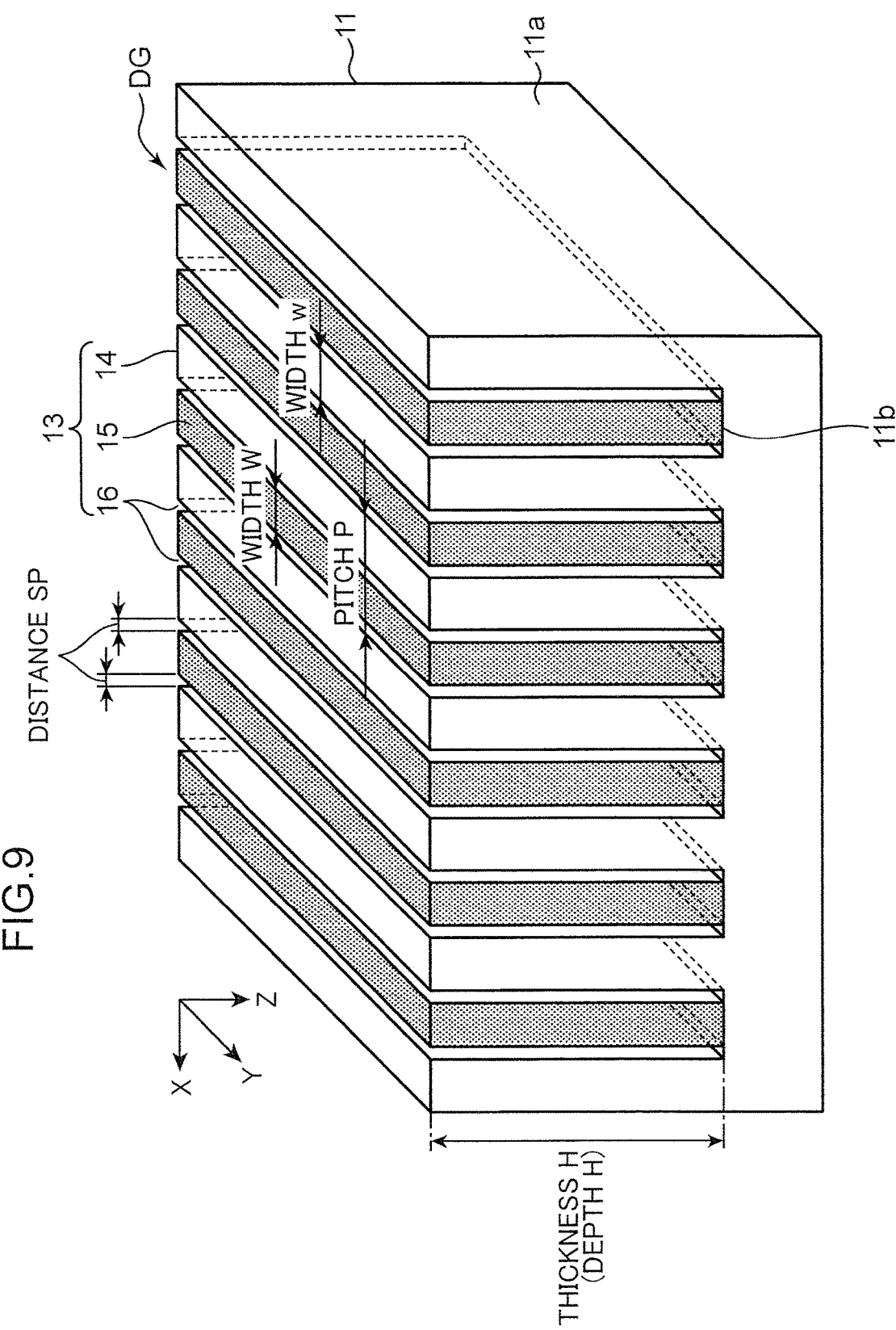
FIG. 9 is a perspective view depicting a configuration of a grating-forming workpiece pertaining to the first embodiment.

Examples of the grating-forming workpiece obtained in the grating forming step include the grating-forming workpiece 11 having the grating region 13, based on the assumption that the grating-forming workpiece 11 and the grating region 13 in FIG. 2 are flat. That is, the grating-forming workpiece 11 may be constructed such that corresponding ones of the plurality of structural portions 14 and the plurality of remaining portions 15 are in contact with each other, as depicted in FIG. 2. Alternatively, it may comprise a void space (air gap) 16 between corresponding ones of the plurality of structural portions 14 and the plurality of remaining portions, as depicted in FIG. 9. FIG. 9 is a perspective view depicting a configuration of another example of the grating-forming workpiece. That is, the grating-forming workpiece 11 having the void spaces (air gaps) 16 comprises: the plurality of structural portions 14; and the plurality of remaining portions 15, wherein each of the air gaps 16 is formed between corresponding ones of the structural portions 14 and the remaining portions 15, in such a manner as to provide a given spacing therebetween in a given planar (in-plane) direction on a grating plane of the grating region 13, and extend along a direction (planar (in-plane) direction) normal to the grating plane of the grating region 13. That is, in the case of a one-dimensional grating structure as in the embodiment depicted in FIG. 9, a plurality of air gaps 16 each providing a given spacing SP in the X direction are provided in the grating region 13 of the grating-forming workpiece 11. In this case, assuming that a width of each of the structural portions 14 is w, and a width of each of the remaining portions 15 is W, an aspect ratio in FIG. 9 is expressed as follows: P=w+W+2×SP. The width w of the structural portion 14 is a length of the structural portion 14 in the X-direction (width direction) orthogonal to the Y direction as the specific direction (longitudinal direction). This grating-forming workpiece 11 having the void space (air gap) between corresponding ones of the structural portions 14 and the remaining portions 16 is a metal grating structure having a grating plane-defining surface with high smoothness (i.e., surface accuracy). The reason is considered as follows. The present inventor found that, in the case where a metal grating structure comprising a metal portion provided as the remaining portion 15 between adjacent two of the structural portions 14 is formed in the grating forming step, when a metal is grown in an electroforming step, a width of the metal portion adjacent to an opening (i.e., top) of a recess becomes slightly greater than a width thereof at a bottom of the recess, and an electroforming stress is generated by the slight difference. Thus, in the grating-forming workpiece 11 having the void space (air gap) 16 formed between corresponding ones of the structural portions 14 and the remaining portions 15 after the plating, it is believed that the generated electroforming stress can be absorbed by the void spaces 16 to enhance smoothness of a grating plane-defining surface thereof.

The grating-forming workpiece 11 having the gaps 16 is a metal grating structure having a grating plane-defining surface with high smoothness (i.e., surface accuracy), as mentioned above. Thus, it is considered that, when such a grating-forming workpiece is used as the grating-forming workpiece before being curved, a curved metal grating structure having a grating plane-defining surface with high smoothness (i.e., surface accuracy) can be manufactured as a curved grating structure. Further, when the grating-forming workpiece 11 having the gaps 16 formed between corresponding ones of the members (structural portions) 14 and the remaining portions (metal portions) 15 is curved, a repulsion force arising from the presence of the metal portion 15 between adjacent two of the members 14 during curvature deformation and acting to hinder the curvature deformation is also absorbed by the gaps 16. From this point of view, a metal grating structure having a grating plane-defining surface with high smoothness (i.e., high surface accuracy) can be manufactured as a curved grating structure.

A production method for the grating-forming workpiece, e.g., the grating forming step, is not particularly limited, as long as it can produce a grating-forming workpiece having the above configuration. A method of producing a metal grating structure 11 as a grating-forming workpiece comprising the gaps 16 and the metal portions as the remaining portions will be described below. For example, this metal grating structure 11 can be produced by the following production method. Specifically, first of all, as the grating forming step, the production method comprises a step of forming, on one surface of a grating-forming workpiece made of an electrically-conductive material, a grating region in which a plurality of structural portions mutually having the same shape are periodically provided via a recess. The production method further comprises, between the grating forming step and the stress layer forming step, an insulation layer forming step of forming an insulation layer on a surface of the recess in the grating-forming workpiece, except for a bottom surface of the recess; an electroforming step of applying voltage across the grating-forming workpiece to perform an electroforming process to thereby fill the recess with a metal; and an insulation layer removing step of removing the insulation layer formed on the surface of the recess in the insulation layer forming step, at least in a region intervening between the grating-forming workpiece and the metal filled in the electroforming step.

The aforementioned recesses 11b may be composed, for example, of a plurality of periodically-arranged slit grooves, in the case of a one-dimensional grating structure, or may be composed, for example, of a plurality of periodically-arranged pillar-shaped holes (pillar-shaped openings) in the case of a two-dimensional grating structure. Further, in the case of a two-dimensional grating structure, when the grating-forming workpiece 11 is etched such that a plurality of periodically-arranged pillar-shaped portions are left as the plurality of structural portions 14, the recesses 11b may also be composed of the etched portions. In this case, the recesses themselves may serve as the structural portions, or a remaining part other than the recesses may serve as the structural portions. In the embodiment illustrated in FIG. 9, a remaining part other than the recesses 11b serves as the structural portions 14.

Figure 10A:
FIGS. 10A to 10D are diagrams (I) illustrating a manufacturing method for the grating-forming workpiece pertaining to the first embodiment.

More specifically, first of all, a flat plate-shaped grating-forming workpiece 11 made of a given electrically-conductive material is preliminarily prepared (FIG. 10A). In this embodiment, a silicon substrate 30 is preliminarily prepared as one example of the grating-forming workpiece 11. The use of the silicon substrate 30 made of silicon as the grating-forming workpiece 11 makes it possible to utilize so-called "silicon fabrication techniques" in which microfabrication techniques have been almost established, so as to produce a microstructural grating region 13 with a relatively high degree of accuracy, and form a plurality of high-aspect ratio slit grooves SD, as one example of the recesses 11b. Preferably, the silicon substrate 30 is n-type silicon in which most carriers are electrons. The n-type silicon has abundant conduction electrons. Thus, when the silicon is connected to a negative electrode, and a negative potential is applied thereto to cause polarization at a cathode, a so-called "ohmic contact" is established with respect to a plating solution 47 in an aftermentioned electroforming step, and a resulting current flow is likely to cause a reduction reaction, resulting in an increase in metal precipitation.

Then, a plurality of slit grooves SD is formed as the recesses 11b to thereby form, in one principal surface of the silicon substrate 30, a grating region 13 in which a plurality of structural portions 14 mutually having the same shape are periodically provided (grating forming step; FIG. 10B to FIG. 11B).

Figure 10C:
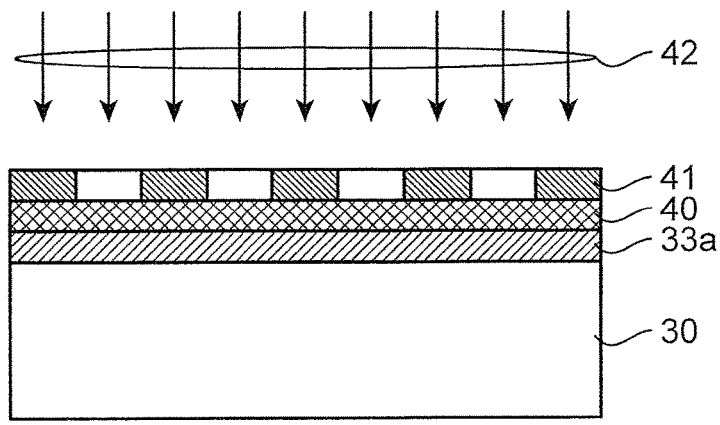
Figure 10D:
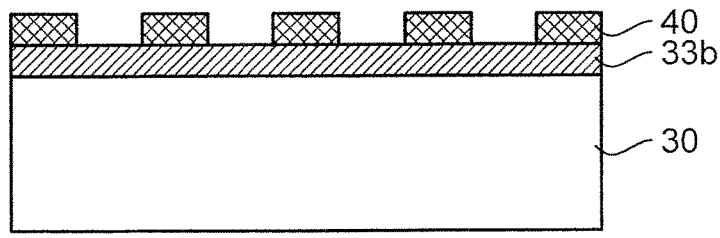
Figure 11A:
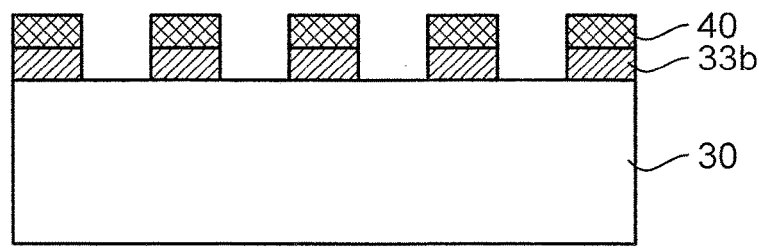
FIGS. 11A to 11D are diagrams (II) illustrating the manufacturing method for the grating-forming workpiece pertaining to the first embodiment.

In one example of the grating forming step, first of all, a resist layer 33a is formed on the principal surface of the silicon substrate 30 (resist layer forming sub-step). Then, this resist layer 33 is patterned, and the patterned portion thereof is removed (patterning sub-step; FIGS. 10C, 10D and 11A). The resist layer means a layer functioning as a protective film against etching during the etching.

For example, the resist layer 33a may be composed of a silicon oxide film (a silicon dioxide film, a quartz film or a SiO$_2$ film) having an insulating property and resistance to a subsequent etching process for the silicon substrate 30. This silicon oxide film 33a is used as the resist layer 33a to be patterned, and a photosensitive resin layer (photoresist film) 40 is used to pattern the silicon oxide film 33a. The term "having resistance" does not mean that an influence of etching is fully eliminated during an etching process, but means that the influence of etching is relatively lowed. This means that during a period of etching a target portion, it is possible to serve as a protective film capable of protecting a non-target portion which should not be etched.

More specifically, the silicon oxide film 33a is formed as the resist layer 33a on a surface of the silicon substrate 30. The silicon oxide film 33a is formed by any one of heretofore-known commonplace means, such as a thermal oxidation process, a chemical vapor deposition process, an anodic oxidation processor, and other deposition process (other vapor deposition process or a sputtering process). As one example, in the thermal oxidation process, an oxygen atmosphere (which may contain inert gas) or water vapor is introduced into a quartz tube in which the silicon substrate 30 is disposed, and the quartz tube is heated by a heater, so as to heat the silicon substrate 30 to a high temperature in the oxygen atmosphere or in a gaseous atmosphere of the water vapor, so that a silicon oxide film 33a having a given thickness is formed on the surface of the silicon substrate 30. As another example, in the chemical vapor deposition (CVD) process, tetraethoxysilane (TEOS) as one type of organic silane is heated and bubbled by carrier gas to form TEOS gas, and then oxidation gas such as oxygen or ozone, and dilution gas such as helium, are mixed with the TEOS gas, to form raw material gas. Then, the raw material gas is introduced into a CVD apparatus such as a plasma CVD apparatus or a normal-temperature ozone CVD apparatus, and a silicon oxide film 33a having a given thickness is formed on a surface of the silicon substrate 30 inside the CVD apparatus. As yet another example, in the anodic oxidization process, a positive electrode of a power supply is connected to the silicon substrate 30, and a cathode electrode connected to the negative electrode of the power supply and the silicon substrate 30 are immersed in an electrolyte solution. Then, upon supplying current, a silicon oxide film 33a having a given thickness is formed on a surface of the silicon substrate 30. The silicon oxide film 33a is formed at least on an upper surface of the silicon substrate 30. Alternatively, it may also be formed on a back surface and/or a side surface thereof. The use of the silicon oxide film 33a as the resist layer 33a makes it possible to use any one of the heretofore-known commonplace means such as the thermal oxidation process, the chemical vapor deposition process and the anodic oxidation process, and thus relatively easily form the silicon oxide film 33a.

Figure 10B:
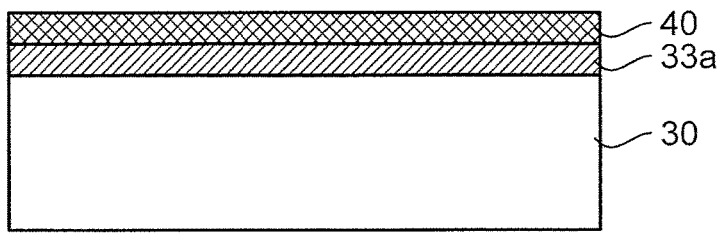

Subsequently, a photosensitive resin layer 40 is formed on the silicon oxide film 33a formed on the silicon substrate 30, for example, by spin coating (FIG. 10B). The photosensitive resin layer 40 used here is a material which is usable in lithography and whose physical properties such as solubility are changed by light (including not only visible light but also ultraviolet light), an electron beam or the like. However, the present invention is not limited thereto. For example, in place of the photosensitive resin layer 40, a resist layer for electron beam exposure may be used. Subsequently, as a photolithography sub-step, the photosensitive resin layer 40 is patterned by a lithography process (FIG. 10C), and the patterned portion of the photosensitive resin layer 40 is removed (FIG. 10D). More specifically, a lithography mask 41 is put on the photosensitive resin layer 40, and ultraviolet light 42 is radiated onto the photosensitive resin layer 40 through the lithography mask 41, so that the photosensitive resin layer 40 is subjected to pattern exposure and development (FIG. 10D). Then, an unexposed portion (or exposed portion) of the photosensitive resin layer 40 is removed (FIG. 10D).

Subsequently, the silicon oxide film 33a is patterned in such a manner that a portion of the silicon oxide film 33a corresponding to a portion of the photosensitive resin layer 40 removed by etching is removed using the patterned photosensitive resin layer 40 as a mask (FIG. 11A). More specifically, the silicon oxide film 33a is patterned, for example, by reactive etching (RIE) using $CHF_3$ gas. Alternatively, the silicon oxide film 33a may be patterned, for instance, by wet etching using hydrofluoric acid. The etching of the silicon oxide film 33a as the resist layer 33a in the patterning sub-step may be performed by any other etching process.

As above, this embodiment, the resist layer (first resist layer) 33a serving as a first pattern mask for etching the silicon substrate 30 is formed, and further the photosensitive resin layer (second resist layer) 40 serving as a second pattern mask for etching the resist layer 33a is formed. Then, in order from the side of the surface, the photosensitive resin layer 40 is patterned using the lithography mask 41, and the resist layer 33a is patterned using the patterned photosensitive resin layer 40 as a mask.

Figure 11B:
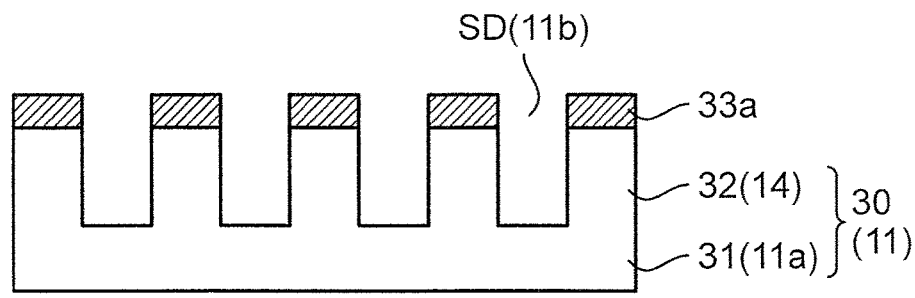

Then, a portion of the silicon substrate 30 corresponding to portions of the photosensitive resin layer 40 and the resist layer 33a removed by dry etching is etched in the Z direction, i.e., the normal direction to reach a given depth H. In this manner, the slit grooves SD (one example of the recesses 11b) is formed (FIG. 11B, etching sib-step).

More specifically, the silicon substrate 30 is etched by ICP (Inductively Coupled Plasma) dry etching to the given depth H from the surface of the silicon substrate 30, using the patterned photosensitive resin layer 40 and resist layer 33a as a mask. Through this ICP dry etching, the photosensitive resin layer 40 is removed. Further, the resist layer 33a may also be slightly etched.

The ICP dry etching is capable of performing vertical etching with a high aspect ratio. Thus, it is preferably an ASE process using an ICP apparatus. The ASE (Advanced Silicon Etch) process is configured to repeatedly perform a step of etching a silicon substrate by RIE (reactive ion etching) using F radicals and F ions in $SF_6$ plasma, and a step of depositing a polymer film having a composition close to Teflon (trademark) on a wall surface through a polymerization reaction of $CF_X$ radicals and ions thereof in $C_4F_8$ plasma to act as a protective film. Further, in view of the capability of performing vertical etching with a high aspect ratio, it is more preferable to alternately perform a side wall protection and a bottom surface etching by alternately repeating a $SF_6$ plasma rich state and a $C_4F_8$ plasma rich state, as in a Bosch process. The dry etching process is not limited to the ICP dry etching, but may be any other technique. For example, an etching technique may be parallel plate type reactive ion etching (RIE), magnetic neutral line plasma (NLD) dry etching, chemically assisted ion beam (CAIB) etching, or electron cyclotron resonance reactive ion beam (ECRIB) etching.

A plate-shaped portion (layer-shaped portion or wall portion) 32 of the silicon substrate 30 remaining along the Y-Z plane after the etching is formed as the plurality of structural portions 14, and a plate-shaped portion (base portion) 31 of the silicon substrate 30 remaining along the X-Y plane after the etching is formed as the base plate portion 11a.

Figure 11C:
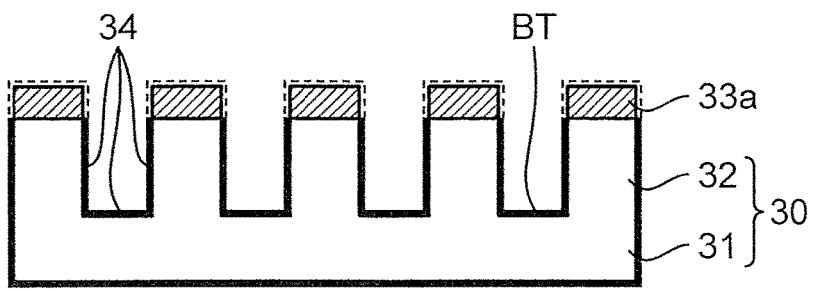
Figure 11D:
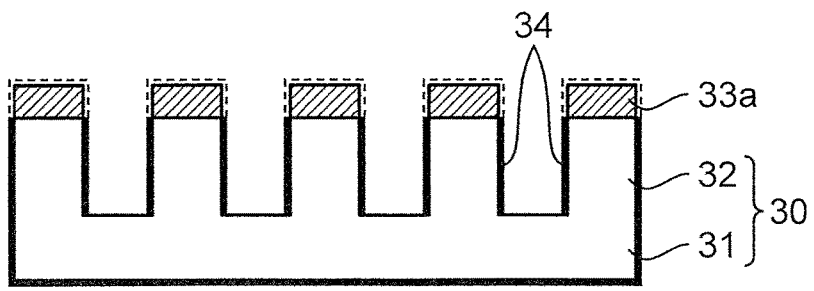

Then, an insulation layer is formed at least on surfaces of the slit grooves SD (recesses 11b) of the silicon substrate 30 (grating-forming workpiece 11), except for bottom surfaces of the slit grooves SD (insulation layer forming step; FIGS. 11C and 11D).

More specifically, first of all, an insulation layer 34 having a thickness is formed at least over the entire inner surface of each of the slit grooves SD of the silicon substrate 30 to have an insulating property against an electroforming process in the aftermentioned electroforming step (FIG. 11C, insulation layer forming sub-step). This insulation layer 34 may be formed by any heretofore-known commonplace means such as a deposition process, a sputtering process or the like for forming a film of a given insulation material. In this embodiment, the silicon substrate 30 is used, and therefore the insulation layer 34 is a silicon oxide film 34. For example, this silicon oxide film is formed using the aforementioned thermal oxidation process or anodic oxidation process. In the case of forming the insulation layer 34 using the thermal oxidation process, it is possible to form, as the insulation layer 34, a silicon oxide film 34 which is dense and excellent in adhesion, and relatively easily control a film thickness thereof. In the case of forming the insulation layer 34 using the anodic oxidation process, it is possible to form. as the insulation layer 34, a silicon oxide film 34 which is dense and excellent in adhesion and film thickness uniformity, and relatively easily control a film thickness thereof. Thus, this metal grating structure production method can form an insulation layer 34 capable of being densified with a given thickness, while ensuring electrical insulation against an electroforming process in the electroforming step. In this regard, in the case where the resist layer 33a is a silicon oxide film 33a, almost no oxide film is formed on the resist layer 33a by an influence of the anodic oxidation during the insulation layer forming sub-step. On the other hand, in the case where the insulation layer forming sub-step is performed by a deposition process even when the resist layer 33a is a silicon oxide film 33a, a silicon oxide film 34 is formed on the resist layer 33a, as indicated by the broken line in FIG. 11C.

Then, a portion of the insulation layer 34 formed on a bottom BT of each of the slit grooves SD is removed (removal sub-step; FIG. 11C). More specifically, the portion of the insulation layer 34 formed on the bottom BT of each of the slit grooves SD is removed, for example, by ICP dry etching using $CHF_3$ gas.

In this sub-step, the ICP dry etching has high vertical directionality, so that, at a time when the portion of the insulation layer 34 formed on the bottom portion BT of each of the slit grooves SD is removed, a portion of the insulating layer 34 formed on inner side surfaces of the slit groove SD (a portion of the insulating layer 34 formed on opposite wall surfaces (opposite side surfaces) of each of a plurality of plate-shaped portions 32 of the silicon substrate 30) is left in a state in which it has a sufficient thickness capable of functioning as an insulation layer. The remaining insulating layer 34 formed on the inner side surfaces of the slit groove SD may have a thickness, e.g., a thickness of about 10 nm or more, which is enough to fulfill a function of blocking a voltage to be applied to the plate-shaped portion 32 of the silicon substrate 30 (a function of electrically insulating the plate-shaped portion 32) in the subsequent electroforming step, in cooperation with the resist layer (silicon oxide film) 33a having an insulating property.

Figure 12A:
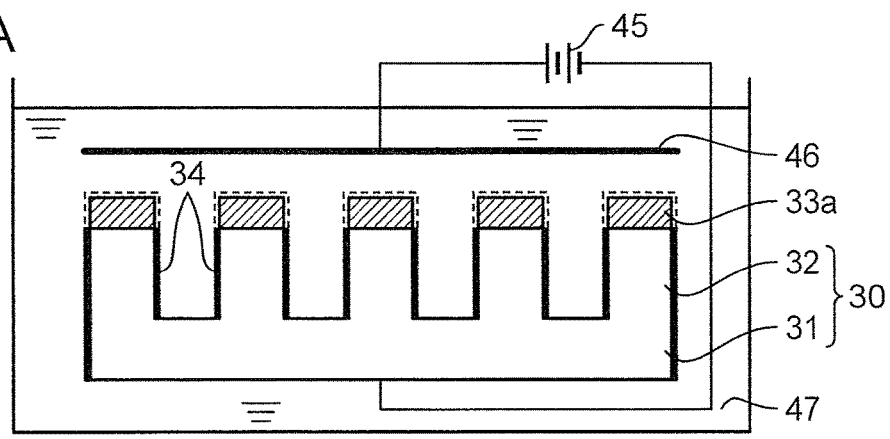
FIGS. 12A to 12C are diagrams (III) illustrating the manufacturing method for the grating-forming workpiece pertaining to the first embodiment.

Then, voltage is applied across the silicon substrate 30 (grating-forming workpiece 11) to perform an electroforming process (electroplating process) to thereby fill each of the slit grooves SD (recesses 11c) with a metal (electroforming step; FIG. 12A). More specifically, a negative electrode of a power supply 45 is connected to the silicon substrate 30, and an anode electrode 46 connected to a positive electrode of the power supply 45 and the silicon substrate 30 are immersed in a plating solution 47. In the case where a silicon oxide film is formed on a portion of the silicon substrate 30 to which the negative electrode of the power supply 45 is connected, the portion is removed in order to achieve conduction between the power supply 45 and the silicon substrate 30. For example, in the case where the silicon oxide film 34 is formed on a surface of the base plate portion 11a of the silicon substrate 30 through the insulation layer forming step, the silicon oxide film 34 formed on the surface of the base plate portion 11a of the silicon substrate 30 is removed, for example, by dry etching, so as to achieve electrical connection between the power supply 45 and the silicon substrate 30. After that, the negative electrode of the power supply 45 is connected to the surface of the base plate portion 11a of the silicon substrate 30. Thus, through electroforming, a metal precipitates and grows from the side of the silicon substrate 30 (plate-shaped portion 31) at the bottoms of the slit grooves SD.

Figure 12B:
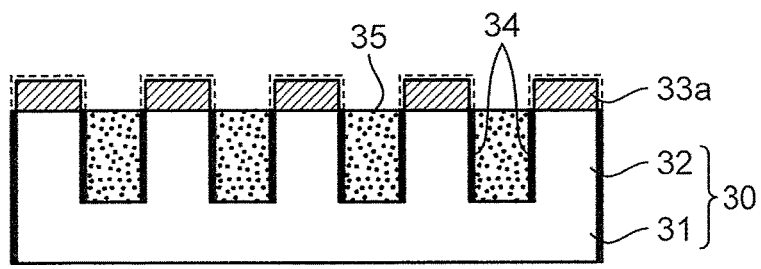

Then, when the slit grooves SD are filled with the metal 35, the electroforming is terminated (FIG. 12B). In this way, metal 35 grows by the same thickness H as that of the plate-shaped portions 32 of the silicon substrate 30. Thus, each of the slit grooves SD is filled with the metal 35 to form the remaining portion 15 composed of a metal portion 35. Preferably, the metal 35 is at least one selected from the group consisting of gold (Au), platinum (Pt), iridium (Ir) and rhodium (Rh), which are preferred examples of a metal having a relatively large atomic weight. These metals relatively largely act to X-rays, so that it becomes possible to reduce the depth H of each of the recesses 11b. Therefore, the above metal grating structure production method can easily produce a grating structure.

Figure 12C:
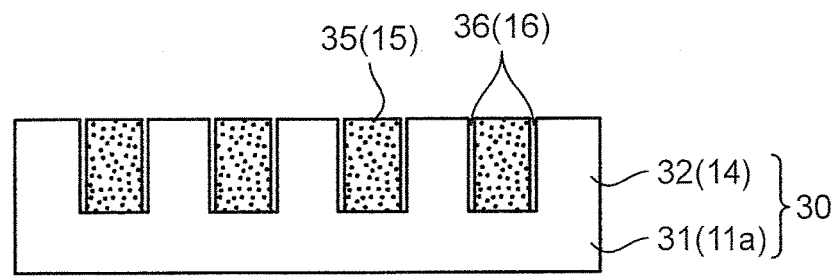

Then, the insulation layer 34 formed on the inner surface of each of the slit grooves SD (recesses 11b) formed in the insulation layer forming step is removed at least in a region intervening between corresponding ones of the plate-shaped portions 32 of the silicon substrate 30 (structural portions 14 of the grating-forming workpiece 11) and the metal portions 35 (remaining portions 15) filled in the electroforming step (insulation layer removing step; FIG. 12C). More specifically, the silicon substrate 30 (grating-forming workpiece 11) after being subjected to the electroforming step is immersed in a hydrofluoric acid solution capable of solving the silicon oxide film 34. As a result, a portion of the insulation layer 34 intervening between corresponding ones of the plate-shaped portions 32 of the silicon substrate 30 and the metal portions 35 is removed, so that an air gap 36 serving as the air gap 13 is formed between corresponding ones of the plate-shaped portions 32 of the silicon substrate 30 and the metal portions 35 filled in the electroforming step, in such a manner as to provide a given first spacing therebetween in a given planar (in-plane) direction on a grating plane X-Y of the grating region 13 (in a one-dimensional grating structure as in the embodiment depicted in FIG. 9, in the X direction), and extend along the Z direction normal to the grating plane X-Y of the grating region 13. The silicon oxide film 33a i.e., the resist layer 33a formed on the top of the plate-shaped portion 32 of the silicon substrate 30 is removed.

Through the above production process, the metal grating structure having the configuration depicted in FIG. 9 is produced.

Next, another embodiment will be described.

Second Embodiment; Grating Unit

In many cases, a curved grating structure DG is manufactured using a silicon wafer (silicon substrate) capable of being fabricated using microfabrication techniques which have been almost established, as mentioned above. From a viewpoint of easiness in sourcing, sourcing cost and others, the silicon wafer is preferably a commonly-used 6 inch-diameter (φ6 inch) type. A curved grating structure DG fabricatable from such a 6 inch-diameter slicing wafer has a square shape, about 10 cm on a side (□ about 10 cm), and a grating area of □ 10 cm or less. A grating unit DGU according to the second embodiment is directed to resolving restrictions on the grating area.

Figure 13:
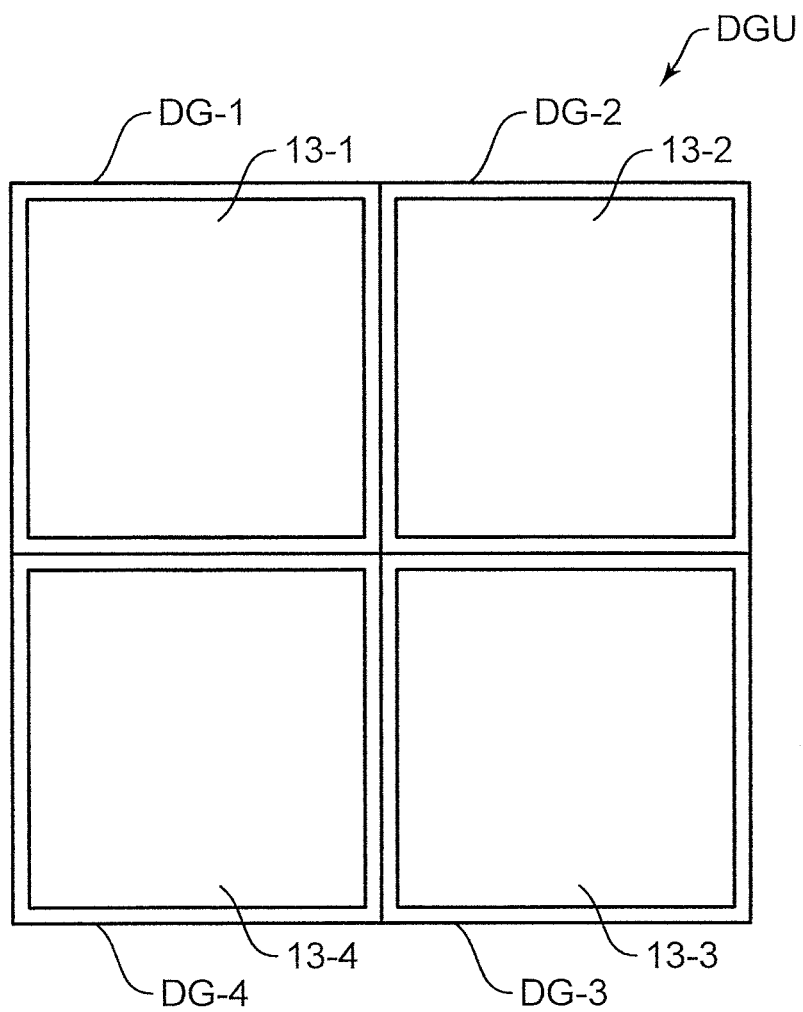
FIG. 13 is a diagram depicting a configuration of a grating unit according to a second embodiment of the present invention.

FIG. 13 is a diagram depicting a configuration of the grating unit according to the second embodiment. In FIG. 13, for the sake of illustration, each of the curved grating structures DG is depicted in a flat state without being curved. Actually, as depicted in FIG. 1, each of the curved grating structures DG is curved by stress.

As depicted in FIG. 13, the X-ray metal grating unit DGU according to the second embodiment comprises a plurality of curved grating structures DG arranged to form one grating plane, wherein at least one of the plurality of curved grating structures DG is composed of the curved grating structure DG according to the first embodiment.

More specifically, in the embodiment depicted in FIG. 13, the grating unit DGU comprises four curved grating structures DG according to the first embodiment. The four curved grating structures DG according to the first embodiment are arranged in two linear and independent directions, more specifically, in the embodiment illustrated in FIG. 13, in two mutually orthogonal directions and in a 2-row×2-column matrix pattern, to allow four grating planes 13-1 to 13-4 to form one grating plane. That is, in a first direction (X direction) with respect to a curved grating structure DG-1 disposed at a 1st row and 1st column position, a curved grating structure DG-2 is disposed at a 1st row and 2nd column position, in adjacent relation to the curved grating structure DG-1, in such a manner that one peripheral side (one of two ends opposed in the X direction) thereof comes into contact with one peripheral side of the curved grating structure DG-1. In a second direction (Y direction) orthogonal to the first direction (X direction) with respect to the curved grating structure DG-1, a curved grating structure DG-4 is disposed at a 2nd row and 1st column position, in adjacent relation to the curved grating structure DG-1, in such a manner that one peripheral side (one of two ends opposed in the Y direction) thereof comes into contact with one peripheral side of the curved grating structure DG-1. Further, in an orthogonal direction with respect to the curved grating structure DG-1, a curved grating structure DG-3 is disposed at a 2nd row and 2nd column position, in adjacent relation to the curved grating structure DG-2 and the curved grating structure DG-4, in such a manner that one peripheral side (one of two ends opposed in the Y direction) thereof comes into contact with one peripheral side of the curved grating structure DG-2, and another peripheral side (one of two ends opposed in the Y direction) thereof comes into contact with one peripheral side of the curved grating structure DG-4.

In the second embodiment, there is provided a grating unit DGU comprising the curved grating structure DG according to the first embodiment, wherein it is possible to obtain a grating plane greater than a grating plane of the one curved grating structure DG. Particularly, in the case where the curved grating structure DG is used in an X-ray diagnostic device, in connection with a required diagnosable area per shot, it is necessary to ensure a certain level of size, e.g., a square, 20 cm or more on a side (□ 20 cm or more). The grating unit DGU according to the second embodiment can meet such a need of the X-ray diagnostic device. That is, in this grating unit, each of the curved grating structures DG can be disposed along a curve, so that it is possible to obtain a grating plane greater than a grating plane of the one curved grating structure DG, while reducing so-called "vignetting".

Next, two other embodiments of the present invention will be described.

Third and Fourth Embodiments: Talbot Interferometer and Talbot-Lau Interferometer As an example of application of the above curved grating structure DG and grating unit DGU, they can be suitably used in an X-ray Talbot interferometer and a Talbot-Lau interferometer. In a refraction grating used in an X-ray Talbot interferometer or Talbot-Lau interferometer, it is necessary that a plurality of structural portions are periodically provided with a period of several μm to several ten μm. For this reason, the manufacturing method for the curved grating structure DG according to the first embodiment (including any modification thereof) is suitable for manufacturing of a metal grating structure used in an X-ray Talbot interferometer or Talbot-Lau interferometer having such micro-sized periodical structural portions. The following description will be made about an X-ray Talbot interferometer or Talbot-Lau interferometer using a curved grating structure DG manufactured by the above manufacturing method, or the grating unit DGU according to the second embodiment, comprising a plurality of the curved grating structures DG.

Figure 14:
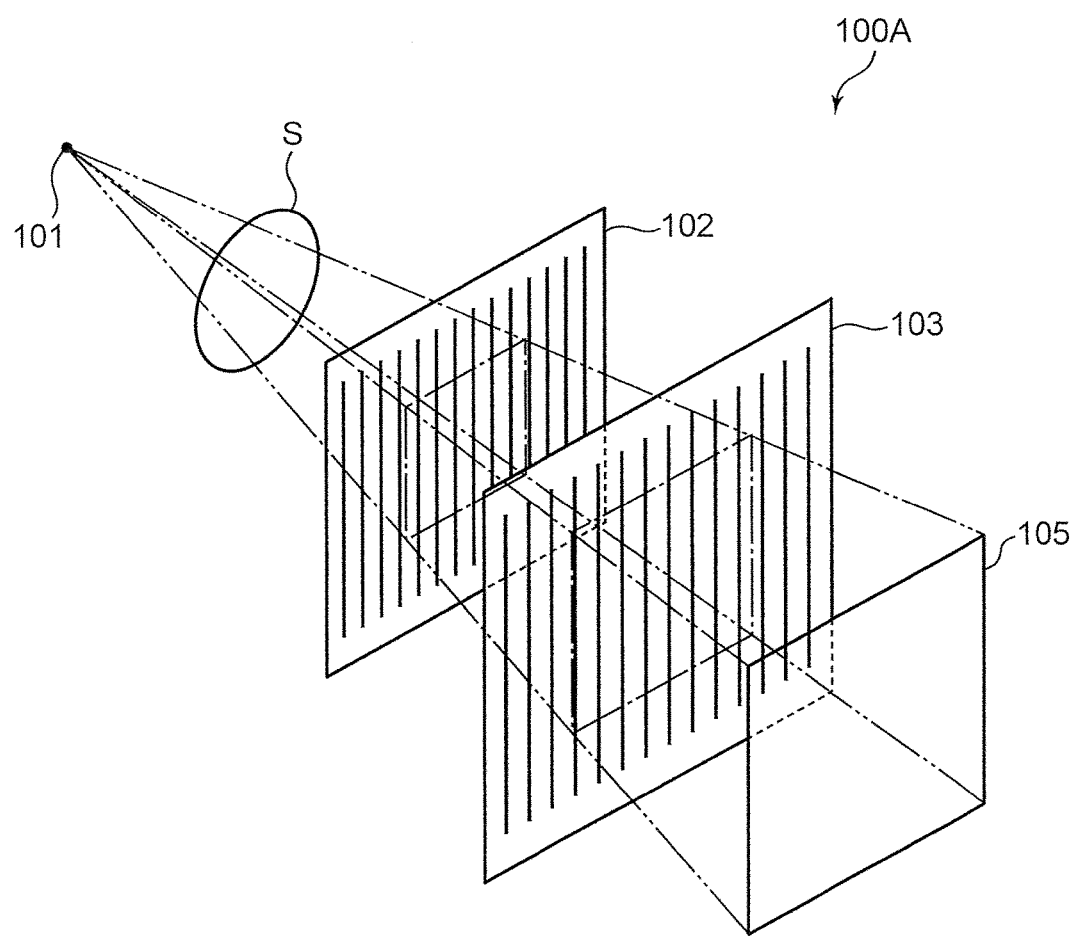
FIG. 14 is a perspective view depicting a configuration of an X-ray Talbot interferometer according to a third embodiment of the present invention.
Figure 15:
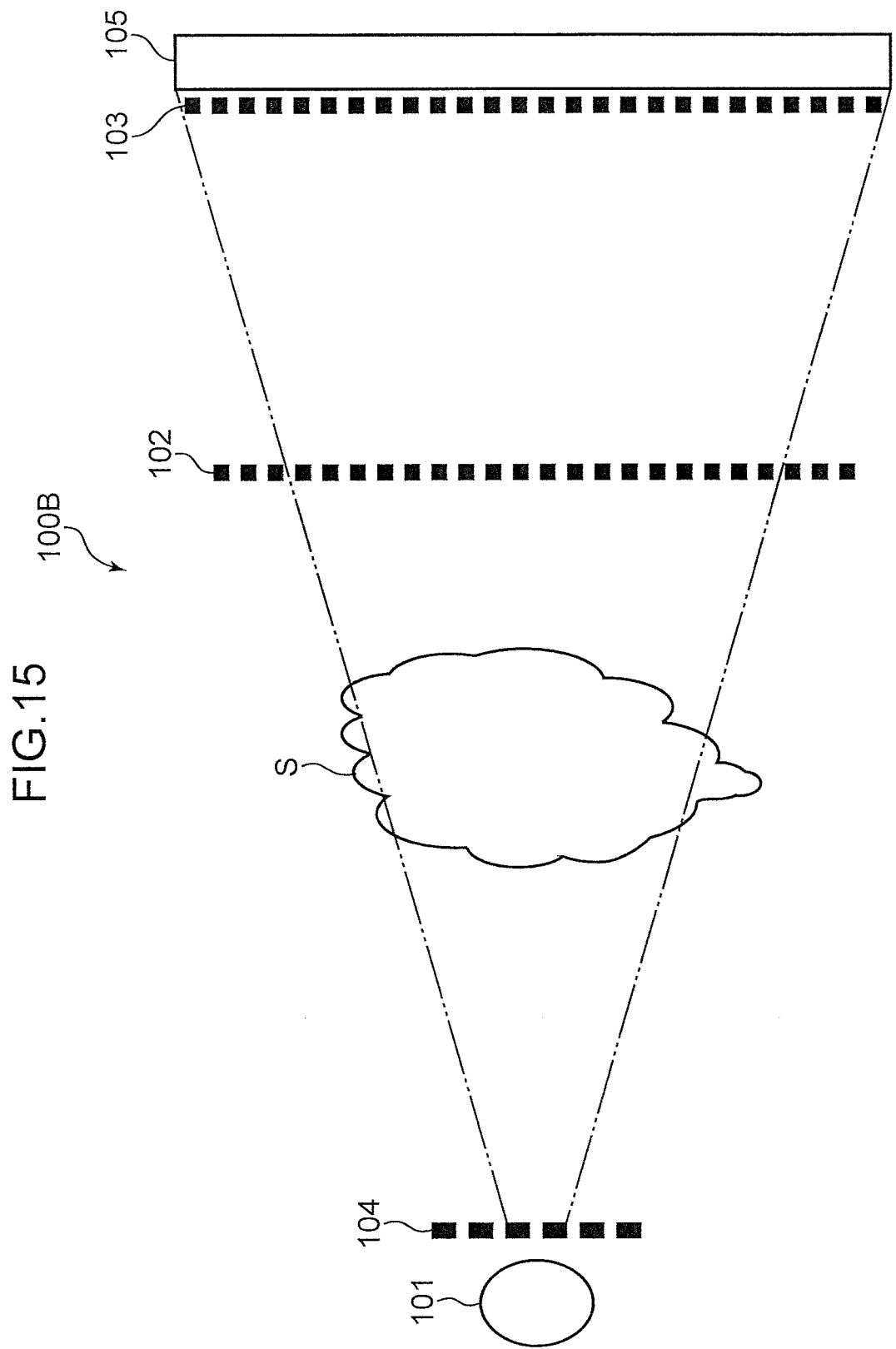
FIG. 15 is a top view depicting a configuration of an X-ray Talbot-Lau interferometer according to a fourth embodiment of the present invention.

FIG. 14 is a perspective view depicting a configuration of an X-ray Talbot interferometer according to a third embodiment of the present invention. FIG. 15 is a top view depicting a configuration of an X-ray Talbot-Lau interferometer according to a fourth embodiment of the present invention.

As depicted in FIG. 14, the X-ray Talbot interferometer 100A according to the third embodiment comprises: an X-ray source 101 configured to radiate X-rays having a given wavelength; a first diffraction grating 102 which is a phase type configured to diffract the X-rays radiated from the X-ray source 101; and a second diffraction grating 103 which is an amplitude type configured to diffract the X-rays diffracted by the first diffraction grating 102 to thereby form an image contrast, wherein the first and second diffraction gratings 102, 103 are set to satisfy conditions for constructing an X-ray Talbot interferometer. The X-rays having an image contrast generated by the second diffraction grating 103 are detected, for example, by an X-ray image detector 105 operable to detect X-rays.

In the X-ray Talbot interferometer 100A, at least one of the first diffraction grating 102 and the second diffraction grating 103 has the aforementioned curved grating structure DG (including any modification thereof), or the aforementioned grating unit DGU. In this case, the at least one diffraction grating can be constructed to be curved along a spherical wave from a spot wave source so as to reduce the so-called "vignetting". Further, in the case where the at least one diffraction grating is composed of the grating unit DGU, the grating unit DGU comprising the plurality of curved grating structures DG can be disposed along a curve, so that it becomes possible to form a larger grating plane while reducing the so-called "vignetting".

The conditions for constructing the Talbot interferometer 100A are expressed by the following formulas 1, 2. The formula 2 is based on an assumption that the first diffraction grating 102 is a phase-type diffraction grating.

$$l = \lambda/(a/(L+Z1+Z2)) \quad \text{formula (1)}$$

$$Z1 = (m+\tfrac{1}{2}) \times (d2/\lambda) \quad \text{formula (2),}$$

where: l denotes a coherence length; A denotes a wavelength of X-rays (generally, center wavelength); a denotes an aperture diameter of the X-ray source 101 in a direction approximately orthogonal to a diffraction member of a diffraction grating; L denotes a distance from the X-ray source 101 to the first diffraction grating 102; Z1 denotes a distance from the first diffraction grating 102 to the second diffraction grating 103; Z2 denotes a distance from the second diffraction grating 103 to the X-ray image detector 105; m denotes an integer; and d denotes a period of a diffraction member (a period of a diffraction grating, a grating constant, a distance between centers of adjacent diffraction members, or the pitch P).

In the X-ray Talbot interferometer 100A having the above configuration, X-rays are radiated from the X-ray source 101 toward the first diffraction grating 102. The radiated X-rays produce a Talbot effect through the first diffraction grating 102 to thereby form a Talbot image. The Talbot image forms an image contrast having moire fringes by an action received through the second grating 103. Then, the image contrast is detected by the X-ray image detector 105.

The Talbot effect means that, upon incidence of light onto the diffraction grating, an image identical to the diffraction grating (a self image of the diffraction grating) is formed at a position away from the diffraction grating by a certain distance, wherein the certain distance is called "Talbot distance L" and the self image is called "Talbot image". In the case where the diffraction grating is a phase-type diffraction grating, the Talbot distance L becomes Z1 (L=Z1) as expressed by the formula 2. The Talbot image appears as a reverted image when the Talbot distance is equal to an odd multiple of L (=(2m+1)), where each of L and m is an integer), and appears as a normal image when the Talbot distance is equal to an even multiple of L (=2 mL).

In the case, when a subject S is disposed between the X-ray source 101 and the first diffraction grating 102, the moire fringes are modulated by the subject S, and an amount of the modulation is proportional to an angle at which X-rays are bent by a refraction effect arising from the subject S. Thus, the subject S and an internal structure of the subject S can be detected by analyzing the moire fringes.

In the Talbot interferometer 100A configured as depicted in FIG. 14, the X-ray source 101 is a single spot light source (spot wave source). Such a single spot light source can be constructed by additionally providing a single slit plate formed with a single slit. X-rays radiated from the X-ray source 101 pass through the single slit of the single slit plate, and is radiated toward the first diffraction grating 102 through the subject S. The slit is an elongate rectangular opening extending in one direction.

On the other hand, as depicted in FIG. 15, a Talbot-Lau interferometer 100B is constructed in such a manner that it comprises: an X-ray source 101; a multi-slit plate 104; a first diffraction grating 102; and a second diffraction grating 103. Specifically, the Talbot-Lau interferometer 100B is constructed in such a manner that it comprises, in addition to the Talbot interferometer 100A depicted in FIG. 14, the multi-slit plate 104 having a plurality of slits formed in parallel relation, on an X-ray radiation side of the X-ray source 101.

The multi-slit plate 104 may be the curved grating structure DG or the grating unit DGU. When the curved grating structure DG is used as the multi-slit plate 104, it can be constructed to be curved along a spherical wave from a spot wave source so as to reduce the so-called "vignetting". Particularly, the multi-slit plate 104 is closer to the wave source than the first diffraction grating 102 and the second diffraction grating 103, in terms of distance, and is thereby composed of a grating stricture more steeply curved with a curvature radius less than that of the first diffraction grating 102 and the second diffraction grating 103. On the other hand, in the case where the multi-slit plate 104 is composed of the grating unit DGU, the grating unit DGU comprising the plurality of curved grating structures DG can be disposed along a curve, so that it becomes possible to form a larger grating plane while reducing the so-called "vignetting".

When the Talbot-Lau interferometer 100B is used, an X-ray dose irradiated toward the first diffraction grating 102 through the subject S is increased, as compared to the Talbot interferometer 100A, so that it becomes possible to obtain better moire fringes.

Next, an additional embodiment of the present invention will be described.

Fifth Embodiment: X-Ray Imaging Device

The curved grating structure DG and the grating unit DGU are utilizable in a variety of optical devices, and suitably used, for example, in an X-ray imaging device. In particular, an X-ray imaging device using an X-ray Talbot interferometer is one phase contrast method designed to handle X-rays as waves and detect a phase shift occurring when X-rays penetrates through a subject, to obtain a transmission image of the subject, so that it has an advantage of being able to expect to improve sensitivity about 1,000 times, as compared to an absorption contrast method designed to obtain an image by utilizing differences in magnitudes of X-ray absorption by a subject as contrast, thereby reducing an X-ray dose, for example, to the range of $\frac{1}{100}$ to $\frac{1}{1000}$. In this embodiment, an X-ray imaging device equipped with an X-ray Talbot interferometer using the aforementioned X-ray metal grating unit DGU will be described.

Figure 16:
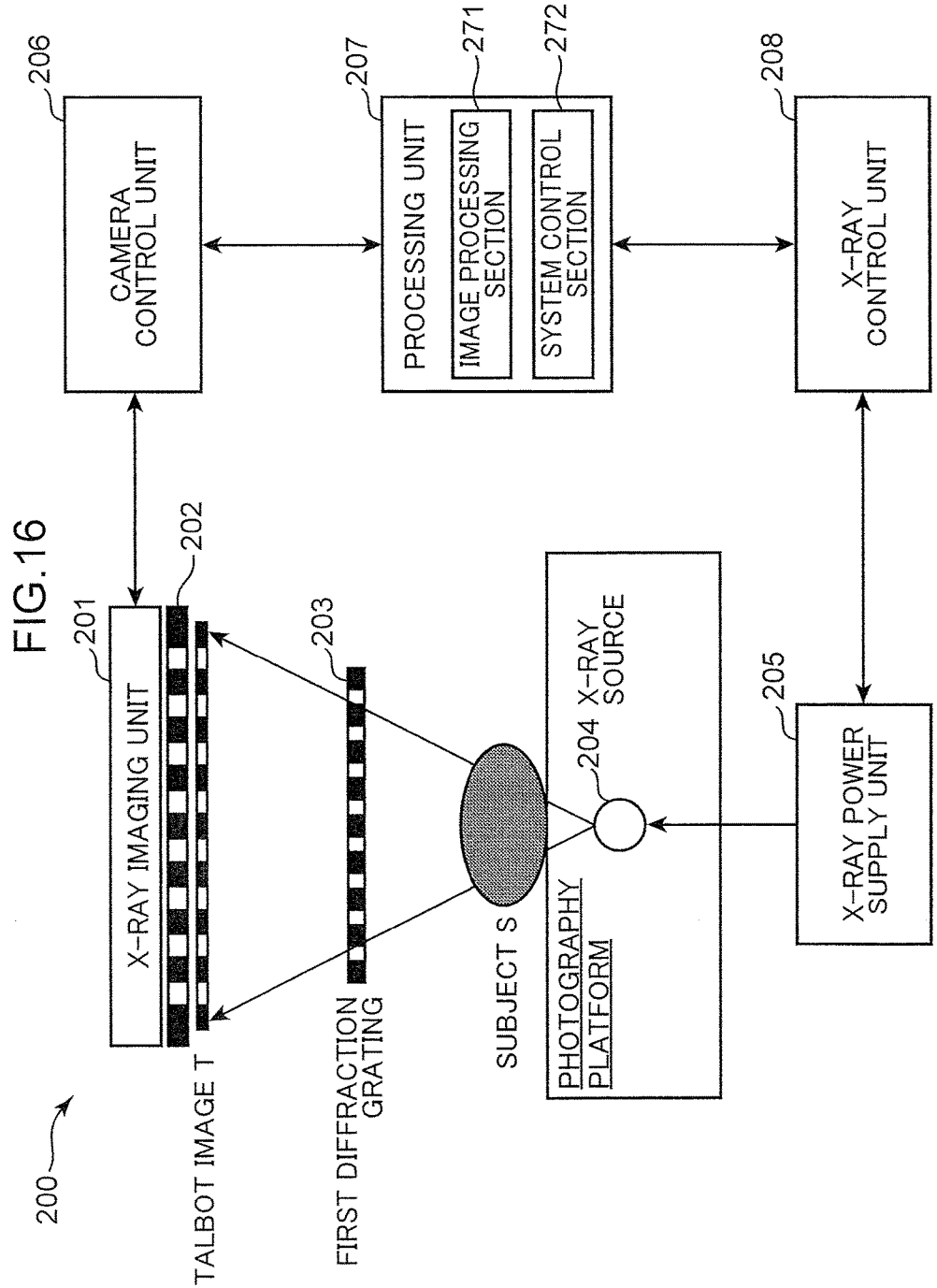
FIG. 16 is an explanatory diagram depicting a configuration of an X-ray imaging device according to a fifth embodiment of the present invention.
Figure 17A:
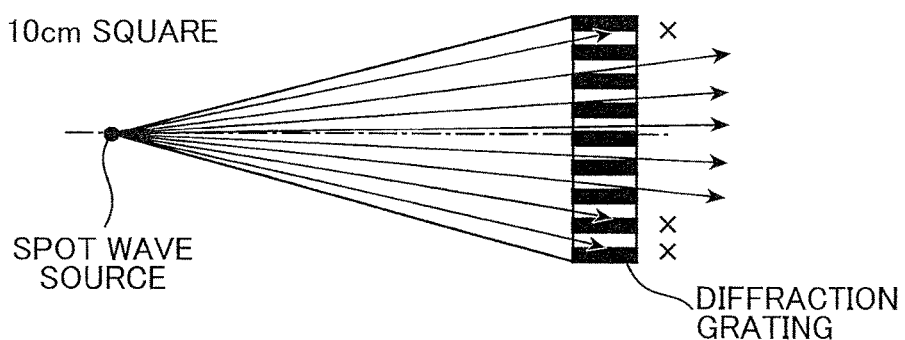
FIGS. 17A and 17B are diagrams illustrating the occurrence of vignetting.
Figure 17B:
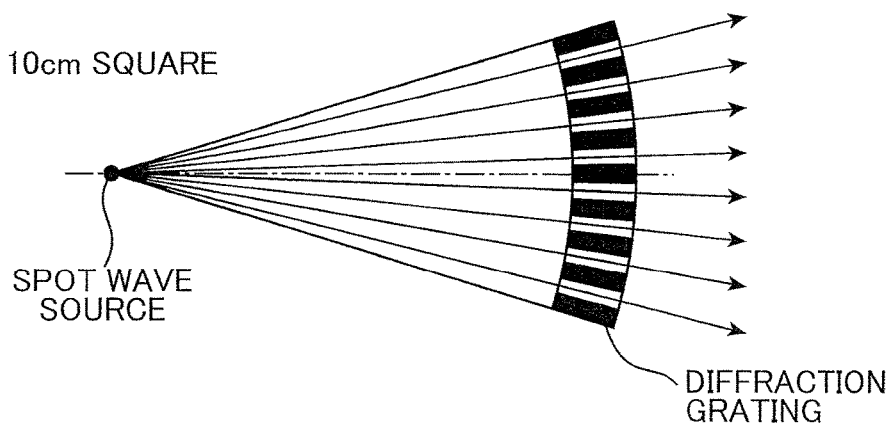

FIG. 16 is an explanatory diagram depicting a configuration of an X-ray imaging device according to a fifth embodiment of the present invention. In FIG. 16, the X-ray imaging device 200 comprises: an X-ray imaging unit 201; a second diffraction grating 202; a first diffraction grating 203; and an X-ray source 204. The X-ray imaging device 200 according to this embodiment further comprises: an X-ray power supply unit 205 for supplying electricity to the X-ray source 204; a camera control unit 206 for controlling an imaging operation of the X-ray imaging unit 201; a processing unit 207 for controlling an overall operation of the X-ray imaging device 200; and an X-ray control unit 208 for controlling an electricity supply operation by the X-ray power supply unit 205 to thereby control an X-ray radiation operation by the X-ray source 204.

The X-ray source 204 is a device operable, in response to receiving electricity supplied from the X-ray power supply unit 205, to radiate X-rays toward the first diffraction grating 203. For example, the X-ray source 204 is a device configured such that a high voltage supplied from the X-ray power supply unit 205 is applied between a cathode and an anode, and electrons released from a filament of the cathode collide with the anode to thereby radiate X-rays.

The first diffraction grating 203 is a diffraction grating configured to produce a Talbot effect by X-rays radiated from the X-ray source 204. For example, the first diffraction grating 203 is composed of the aforementioned grating unit DGU, in order to take an image of the subject S by a larger area. The first diffraction grating 203 is set to satisfy conditions for producing a Talbot effect, and is a phase-type diffraction grating having a sufficiently coarse grating with respect to a wavelength of X-rays radiated from the X-ray source 204, for example, having a grating constant (a period of a diffraction grating) d of about 20 times or more of the wavelength of the X-rays. The first diffraction grating 203 may be an amplitude-type diffraction grating.

The second diffraction grating 202 is a transmission and amplitude-type diffraction grating disposed at a position away from the first diffraction grating 203 approximately by a Talbot distance L, to diffract X-rays diffracted by the first diffraction grating 203. As with the first diffraction grating 203, the second diffraction grating 202 is composed, for example, of the aforementioned grating unit DGU.

Preferably, in the first diffraction grating 203, the plurality of curved grating structures DG constituting the first diffraction grating 203 are arranged along a vertical cylindrical surface having an axis defined by a virtual line passing through a radiation source of the X-ray source 204 as a spot light source, in such a manner that a normal line passing through a center of a light-receiving surface (grating plane) of each of the X-ray metal grating structures DG passes through the radiation source of the X-ray source 204, and the light-receiving surface (grating plane) has contact with the virtual cylindrical surface. Preferably, in the second diffraction grating 202, the plurality of X-ray metal grating structures DG constituting the second diffraction grating 202 are arranged along a vertical cylindrical surface having an axis defined by a virtual line passing through a radiation source of the X-ray source 204 as a spot light source, in such a manner that a normal line passing through a center of a light-receiving surface (grating plane) of each of the X-ray metal grating structures DG passes through the radiation source of the X-ray source 204, and the light-receiving surface (grating plane) has contact with the virtual cylindrical surface.

The first diffraction grating 203 may be the aforementioned curved grating structure DG, and the second diffraction grating 202 may be the aforementioned curved grating structure DG.

The first and second diffraction gratings 203, 202 are set to satisfy conditions for constructing a Talbot interferometer expressed by the aforementioned formulas 1 and 2.

The X-ray imaging unit 201 is a device for imaging an image of X-rays diffracted by the second diffraction grating 202. For example, the X-ray imaging unit 201 is a flat panel detector (FPD) comprising a two-dimensional image sensor in which a thin film layer containing a scintillator for absorbing X-ray energy and emitting fluorescence is formed on a light receiving surface, or an image intensifier camera comprising: an image intensifier unit for converting incident photons into electrons by a photoelectric surface, and after doubling the electrons by a micro-channel plate, causing the group of doubled electron to collide with a fluorescent material to generate fluorescence; and a two-dimensional image sensor for imaging output light from the image intensifier unit.

The processing unit 207 is a device for by controlling units of the X-ray imaging device 200 to thereby control the overall operation of the X-ray imaging device 200. For example, the processing unit 207 is constructed in such a manner that it comprises a microprocessor and peripheral circuits thereof, and functionally comprises an image processing section 271 and a system control section 272.

The system control section 272 is operable to transmit and receive control signals with respect to the X-ray control unit 208 to thereby control an X-ray radiation operation of the X-ray source 204 through the X-ray power supply unit 205, and transmit and receive control signals with respect to the camera control unit 206 to thereby control an imaging operation of the X-ray imaging unit 201. Under control of the system control section 272, X-rays are irradiated toward the subject S. Then, a resulting image is taken by the X-ray imaging unit 201, and an image signal is input into the processing unit 207 via the camera control unit 206.

The image processing section 271 is operable to process the image signal generated by the X-ray imaging unit 201, and generate an image of the subject S.

An operation of the X-ray imaging device 200 according to this embodiment will be described. For example, a subject S is placed on a photography platform provided with the X-ray source 204 internally (or on the back thereof), and thereby disposed between the X-ray source 204 and the first diffraction grating 203. When a user (operator) of the X-ray imaging device 200 issues an instruction for imaging the subject S, from a non-depicted operation section, the system control section 272 in the processing unit 207 outputs a control signal to the X-ray control unit 208 for radiating X-rays to the subject S. According to this control signal, the X-ray control unit 208 instructs the X-ray power supply unit 205 to supply electricity to the X-ray source 204, and thus the X-ray source 204 radiates X-rays toward the subject S.

The radiated X-rays passes through the first diffraction grating 203 through the subject S, and is diffracted by the first diffraction grating 203, whereby a Talbot image T as a self image of the first diffraction grating 203 is formed at a position away from the first diffraction grating 203 by a Talbot distance L (=Z1).

The formed Talbot image T of X-rays is diffracted by the second diffraction grating 202, and an image of resulting moire fringes is formed. The image of moire fringes is imaged by the X-ray imaging unit 201 whose parameter such as exposure time is controlled by the system control section 272.

The X-ray imaging unit 201 outputs an image signal indicative of an image of moire fringes, to the processing unit 207 via the camera control unit 206. The image signal is processed by the image processing section 271 in the processing unit 207.

The subject S is disposed between the X-ray source 204 and the first diffraction grating 203. Thus, a phase of X-rays passing through the subject S is shifted from a phase of X-rays which does not pass through the subject S. As a result, X-rays entering the first diffraction grating 203 includes distortion in a wave front thereof, and a Talbot image T is deformed accordingly. Thus, the moire fringes of an image generated by overlapping the Talbot image T and the second diffraction grating 202 undergo modulation by the subject S, and an amount of the modulation is proportional to an angle at which the X-ray is bent by a refraction effect by the subject S. Therefore, the subject S and the internal structure of the subject S can be detected by analyzing the moire fringes. Further, the subject S may be imaged from different angles so as to form a tomographic image of the subject S by phase-contrast X-ray computed tomography (CT).

The second diffraction grating 202 in this embodiment is the X-ray metal grating unit DGU comprising the X-ray metal grating structures DG according to the first embodiment, each having high-aspect ratio metal portions. Thus, it is possible to obtain good moire fringes, thereby obtaining a highly-accurate image of the subject S.

Further, in the case where the curved grating structures DG of the grating unit DGU are formed by subjecting a silicon wafer to dry etching using a Bosch process, a side surface of each of the recesses becomes more flat, and therefore the second diffraction grating 202 can be formed with a high degree of accuracy. Thus, it is possible to obtain better moire fringes, thereby obtaining a further highly-accurate image of the subject S.

In the above X-ray imaging device 200, a Talbot interferometer is composed of the X-ray source 204, the first diffraction grating 203, and the second diffraction grating 202. Alternatively, a Talbot-Lau interferometer may be constructed by additionally disposing the aforementioned X-ray metal grating structure DG as a multi-slit member on the X-ray radiation side of the X-ray source 204. Based on such a Talbot-Lau interferometer, an X-ray dose to be radiated to the subject S can be increased, as compared to the case where a single slit member is used. This makes it possible to obtain better moire fringes, thereby obtaining a further highly-accurate image of the subject S.

In the above X-ray imaging device 200, a subject S is disposed between the X-ray source 204 and the first diffraction grating 203. Alternatively, a subject S may be disposed between the first diffraction grating 203 and the second diffraction grating 202.

In the above X-ray imaging device 200, an image of X-rays is taken by the X-ray imaging unit 201, and electronic data of the image is obtained. Alternatively, an image of X-rays may be obtained by an X-ray film.

The specification discloses the aforementioned features. The following is a summary of the primary features of the embodiments.

According to one aspect of the present invention, there is provided a method for manufacturing a curved grating structure. The method comprises: a grating forming step of forming, in one surface of a grating-forming workpiece, a grating region in which a plurality of members mutually having a same shape are periodically provided; a stress layer forming step of forming a stress layer capable of generating stress, on a grating plane-defining surface of the grating region; a boding step of bonding a support substrate to the stress layer; a polishing step of polishing the other surface of the grating-forming workpiece on a side opposite to the one surface having the support substrate bonded thereto; and a peeling step of peeling off the support substrate from the stress layer, wherein the polishing step is configured to perform the polishing to allow the grating-forming workpiece to be curved by a stress arising from the stress layer, after the peeling step.

The manufacturing method of the present invention makes it possible to manufacture a grating structure steeply curved with a relatively small curvature radius, while suppressing the occurrence of a problem during manufacturing thereof so as to ensure sufficiently high handleability.

The reason is considered as follows.

In the above manufacturing method, first of all, the grating region is formed in one surface of the grating-forming workpiece, and the stress layer is formed on a grating plane-defining surface of the grating region. Subsequently, the support substrate is bonded to the stress layer. That is, just after forming the stress layer, the support substrate is bonded to the stress layer, instead of thinning the grating-forming workpiece by polishing or the like to facilitate curvature deformation in a situation where even after formation of the stress layer, a curvature of the grating-forming workpiece is still insufficient, for example, due to an excessively large thickness of the grating-forming workpiece. Then, after formation of the stress layer, the other surface of the grating-forming workpiece on the side opposite to the one surface is subjected to polishing in such a manner as to allow the grating-forming workpiece to be curved by a stress arising from the stress layer, after peeling the support substrate. Even after the polishing, until the support substrate is peeled off, substrate curvature deformation is suppressed by the bonded support substrate. Then, when the support substrate is peeled off from the stress layer, the grating-forming workpiece is largely curved to obtain a curved grating structure steeply curved with a relatively small curvature radius.

Only after the polishing step, the grating-forming workpiece is thinned enough to cause curvature deformation, and, only after the peeling step, the grating-forming workpiece is actually curved. This makes it possible to minimize an operation to be performed in a situation where the grating-forming workpiece is thinned or curved, thereby sufficiently suppressing the occurrence of a problem such as crack of the grating-forming workpiece during manufacturing. Thus, this manufacturing method can provide enhanced handleability during manufacturing.

During the polishing, the support substrate is bonded to the grating-forming workpiece, and therefore curvature deformation is suppressed. This makes it possible to realize polishing in a state in which the grating-forming workpiece does not have any unwanted curvature deformation. Such desirable polishing can be realized, so that it becomes possible to provide enhanced handleability during manufacturing.

In this manufacturing method, the stress layer is formed on the grating plane-defining surface of the grating-forming workpiece, and therefore the grating plane is maintained in a non-open state after formation of the stress layer, so that it becomes possible to suppress damage or the like to the grating region during manufacturing. In addition, in an obtained curved grating structure, the grating plane thereof is maintained in a non-open state by the stress layer, so that it becomes possible to suppress damage to the grating region.

The curved grating structure obtained by this manufacturing method is steeply curved with a relatively small curvature radius, so that it becomes possible to prevent or reduce so-called "vignetting", even in the case of using a spot wave source. Further, this curved grating structure may be further curved. In this case, a distance with respect to a point wave source can be reduced, thereby facilitating downsizing of a device.

As above, the manufacturing method of the present invention is capable of manufacturing a grating structure steeply curved with a relatively small curvature radius, while suppressing the occurrence of a problem during manufacturing thereof so as to ensure sufficiently high handleability.

Preferably, the manufacturing method of the present invention comprises, between the polishing step and the peeling step, a slitting step of forming a slit from the other surface of the grating-forming workpiece in a normal direction with respect to the other surface, until reaching a depth equal to or greater than a total thickness of the grating-forming workpiece and the stress layer, to thereby form a section surrounded by the slit, in the grating-forming workpiece.

In the manufacturing method having this feature, the slit is formed before the peeling step. Thus, as long as a shape of the section surrounded by the slit formed in the slitting step is a desired shape of a curved grating structure to be manufactured, a curved grating structure having the desired shape can be obtained after the peeling step. In addition, the slitting is performed in the state in which the support substrate is bonded, so that it becomes possible to suppress damage to the grating region and others which would be caused by a situation where a curved grating structure obtained without being subjected to the slitting step is cut into a desired shape. Thus, the above manufacturing method makes it possible to manufacture a curved grating structure having a desired shape, while ensuring high handleability during manufacturing thereof.

Preferably, in the above manufacturing method, the slitting step is configured to form the section surrounded by the slit, plurally.

In the manufacturing method having this feature, in the slitting step, the section surrounded by the slit is formed plurally. Thus, as long as a shape of the section surrounded by the slit formed in the slitting step is a desired shape of a curved grating structure to be manufactured, a plurality of curved grating structures each having the desired shape can be obtained after the peeling step, at one time. Further, in the case where each of a plurality of small-size grating structures without being curved (e.g., without a stress layer) is formed as a curved grating structures, it is necessary to cause them to become curved, individually. In contrast, this manufacturing method can eliminate the need to cause a plurality of small-size grating structures to become curved, individually. In addition, the slitting is performed in the state in which the support substrate is bonded, so that it becomes possible to suppress damage to curved grating structures which would be caused by a situation where a curved grating structure obtained without being subjected to the slitting step is cut into a plurality of pieces. Further, a plurality of curved grating structures each having a desired shape can be manufactured at one time, so that it becomes possible to efficiently manufacture a plurality of small-size curved grating structures, as compared to the case where a curved grating structure obtained without being subjected to the slitting step is cut into a plurality of pieces. Thus, the above manufacturing method makes it possible to simultaneously manufacture a plurality of small-size curved grating structures each having a desired shape, while ensuring high handleability during manufacturing thereof.

Preferably, in the manufacturing method of the present invention, the grating forming step is configured to form the grating region by forming a recess, wherein the method comprises, between the grating forming step and the stress layer forming step, an insulation layer forming step of forming an insulation layer on a surface of the recess in the grating-forming workpiece, except for a surface of a bottom of the recess, an electroforming step of applying voltage across the grating-forming workpiece to perform an electroforming process to fill the recess with a metal, and an insulation layer removing step of removing the insulation layer formed on the surface of the recess in the insulation layer forming step, at least in a region intervening between the grating-forming workpiece and the metal filled in the electroforming step.

The manufacturing method having this feature makes it possible to manufacture, as a curved grating structure, a metal grating structure having a grating plane-defining surface with high smoothness (i.e., surface accuracy).

Specifically, the present inventor found a phenomenon that, in the case where a metal grating structure comprising a metal portion provided between adjacent two of the members is formed in the grating forming step, when a metal is grown in the electroforming step, a width of the metal portion adjacent to an opening (i.e., top) of the recess becomes slightly greater than a width thereof at a bottom of the recess. Then, an electroforming stress is generated by the slight difference in width between the bottom and the top. The present inventor found that the electroforming stress causes a strain in a metal grating structure and thus deterioration in smoothness of the grating plane-defining surface. In this manufacturing method, an air gap is formed between corresponding ones of the members and the metal portions each formed in the recess between adjacent two of the members, so that the electroforming stress occurring in the grating region can be absorbed by the air gaps. Therefore, smoothness of a grating plane-defining surface of the grating structure before being curved is enhanced. This grating structure having a grating plane-defining surface with high smoothness is curved. Thus, it is considered that a metal grating structure having a grating plane-defining surface with high smoothness (i.e., high surface accuracy) can be manufactured as a curved grating structure.

Further, the grating-forming workpiece having the gap between corresponding ones of the members and the metal portions is curved. Thus, a repulsion force arising from the presence of the metal portion between adjacent two of the members during curvature deformation and acting to hinder the curvature deformation is also absorbed by the gaps.

As above, it is believed that this manufacturing method makes it possible to manufacture, as a curved grating structure, a metal grating structure having a grating plane-defining surface with high smoothness (i.e., surface accuracy).

Preferably, in the manufacturing method of the present invention, the bonding step is configured to bond the stress layer and the support substrate together through a tacky adhesive layer, and the peeling step is configured to lower a tacky adhesive force of the adhesive layer by heating or by ultraviolet irradiation via the support substrate.

In the manufacturing method having this feature, even if, in any step before the peeling step, a tacky adhesive force between the stress layer and the support substrate is relatively high, the tacky adhesive force of the tacky adhesive layer can be lowered in the peeling step by heating or by ultraviolet irradiation via the support substrate, to thereby allow the support substrate to be easily peeled off from the stress layer. Thus, this manufacturing method makes it possible to suppress the occurrence of damage to the grating region during peeling and thus provide more enhanced handleability of the curved grating structure during manufacturing thereof.

According to another aspect of the present invention, there is provided a curved grating structure manufactured by the above manufacturing method.

The curved grating structure in this aspect of the present invention is manufactured by the above manufacturing method is provided. Thus, it becomes possible to provide a curved grating structure steeply curved with a relatively small curvature radius, while suppressing the occurrence of a problem during manufacturing thereof.

According to yet another aspect of the present invention, there is provided a grating unit which comprises a plurality of grating structures arranged to form one grating plane, wherein at least one of the plurality of grating structures is composed of the above curved grating structure.

The grating unit in this aspect of the present invention comprises the plurality of aforementioned grating structures. In this grating unit, each of the curved grating structures can be disposed along a curve, so that it is possible to obtain a grating plane greater than a grating plane of the one curved grating structure, while reducing so-called "vignetting".

According to still another aspect of the present invention, there is provided an X-ray imaging device which comprises: an X-ray source for radiating X-rays; a Talbot interferometer or Talbot-Lau interferometer configured to be irradiated with X-rays radiated from the X-ray source; and an X-ray imaging element for imaging X-rays from the Talbot interferometer or Talbot-Lau interferometer, wherein the Talbot interferometer or Talbot-Lau interferometer comprises the above curved grating structure.

The X-ray imaging device in this aspect of the present invention comprises the aforementioned curved grating structure. In this X-ray imaging device, each of the curved grating structures can be disposed along a curve, so that it is possible to reduce so-called "vignetting". Further, in the case where the curved grating structure is included as the grating unit comprising a plurality of the curved grating structures, it is possible to obtain a grating plane greater than a grating plane of the one curved grating structure, so that it becomes possible to realize an X-ray imaging device having a larger diagnosable area.

This application is based on Japanese Patent Application Serial No. 2013-221986 filed in Japan Patent Office on Oct. 25, 2013, the contents of which are hereby incorporated by reference.

To express the present invention, the present invention has been appropriately and sufficiently described through the embodiments with reference to the drawings above. However, it should be recognized that those skilled in the art can easily modify and/or improve the embodiments described above. Therefore, it is construed that modifications and improvements made by those skilled in the art are included within the scope of the appended claims unless those modifications and improvements depart from the scope of the appended claims.

INDUSTRIAL APPLICABILITY

The present invention provides a curved grating structure manufacturing method capable of manufacturing a grating structure steeply curved with a relatively small curvature radius, while suppressing the occurrence of a problem during manufacturing thereof so as to ensure sufficiently high handleability, and a curved grating structure manufactured by the manufacturing method. The present invention also provides a grating unit constructed by arranging a plurality of the curved grating structures side-by-side, and an X-ray imaging device using the curved grating structure.

LIST OF REFERENCE SIGN

11: grating-forming workpiece
12: stress layer
13: grating region
14: member (structural portion)
15: remaining portion (metal)
16: air gap (gap)
21: support substrate
22: tacky adhesive layer

The invention claimed is:
1. A method for manufacturing a curved grating structure, comprising:
 a grating forming step of forming, in one surface of a grating-forming workpiece, a grating region in which a plurality of members mutually having a same shape are periodically provided;
 a stress layer forming step of forming a stress layer capable of generating stress, on a grating plane-defining surface of the grating region;
 a boding step of bonding a support substrate to the stress layer;
 a polishing step of polishing the other surface of the grating-forming workpiece on a side opposite to the one surface having the support substrate bonded thereto; and
 a peeling step of peeling off the support substrate from the stress layer,
 wherein the polishing step is configured to perform the polishing to allow the grating-forming workpiece to be curved by a stress arising from the stress layer, after the peeling step.
2. The method as recited in claim 1, which comprises, between the polishing step and the peeling step, a slitting step of forming a slit from the other surface of the grating-forming workpiece in a normal direction with respect to the other surface, until reaching a depth equal to or greater than a total thickness of the grating-forming workpiece and the stress layer, to thereby form a section surrounded by the slit, in the grating-forming workpiece.
3. The method as recited in claim 2, wherein the slitting step is configured to form the section surrounded by the slit, plurally.
4. The method as recited in claim 1, wherein the grating forming step is configured to form the grating region by forming a recess, and wherein the method comprises, between the grating forming step and the stress layer forming step,
 an insulation layer forming step of forming an insulation layer on a surface of the recess in the grating-forming workpiece, except for a surface of a bottom of the recess,
 an electroforming step of applying voltage across the grating-forming workpiece to perform an electroforming process to fill the recess with a metal, and
 an insulation layer removing step of removing the insulation layer formed on the surface of the recess in the insulation layer forming step, at least in a region intervening between the grating-forming workpiece and the metal filled in the electroforming step.
5. The method as recited in claim 1, wherein
 the bonding step is configured to bond the stress layer and the support substrate together through a tacky adhesive layer, and
 the peeling step is configured to lower a tacky adhesive force of the tacky adhesive layer by heating or by ultraviolet irradiation via the support substrate.
6. A curved grating structure manufactured by the method as recited in claim 1.
7. A grating unit comprising a plurality of grating structures arranged to form one grating plane, wherein at least one of the plurality of grating structures is composed of the curved grating structure as recited in claim 6.
8. An X-ray imaging device comprising:
 an X-ray source for radiating X-rays;
 a Talbot interferometer or Talbot-Lau interferometer configured to be irradiated with X-rays radiated from the X-ray source; and
 an X-ray imaging element for imaging X-rays from the Talbot interferometer or Talbot-Lau interferometer,
 wherein the Talbot interferometer or Talbot-Lau interferometer comprises the curved grating structure as recited in claim 6.

* * * * *